(12) United States Patent
Nam et al.

(10) Patent No.: US 8,383,631 B2
(45) Date of Patent: Feb. 26, 2013

(54) 1,6-DISUBSTITUTED-3-AMINO-4,5,6,7-TETRAHYDRO-1H-PYRAZOLO[3,4-C]PYRIDIN-7-ONE COMPOUNDS AND PREPARATION THEREOF

(75) Inventors: Ghilsoo Nam, Seoul (KR); Ae Nim Pae, Seoul (KR); Kyung Il Choi, Seoul (KR); Hyunah Choo, Seoul (KR); Vani Nelamane Devegowda, Seoul (KR); Seon Hee Seo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 217 days.

(21) Appl. No.: 12/883,987

(22) Filed: Sep. 16, 2010

(65) Prior Publication Data
US 2011/0319619 A1  Dec. 29, 2011

(30) Foreign Application Priority Data
Jun. 24, 2010  (KR) ........................ 10-2010-0060138

(51) Int. Cl.
*C07D 471/04* (2006.01)
*A61K 31/496* (2006.01)
(52) U.S. Cl. .................... 514/253.04; 544/362; 546/119
(58) Field of Classification Search ........................ None
See application file for complete search history.

(56) References Cited

U.S. PATENT DOCUMENTS
3,423,414 A * 1/1969 Blatter .......................... 546/119

* cited by examiner

*Primary Examiner* — Emily Bernhardt
(74) *Attorney, Agent, or Firm* — Frommer Lawrence & Haug LLP; Ronald R Santucci

(57) ABSTRACT

Provided are a novel 1,6-disubstituted-4,5,6,7-tetrahydro-1H-pyrazolo[3,4-c]pyridin-7-one compound, a pharmaceutically acceptable salt compound thereof, a method for preparing the compound, and an anticancer pharmaceutical composition including the compound as an effective ingredient.

7 Claims, No Drawings

1,6-DISUBSTITUTED-3-AMINO-4,5,6,7-TETRAHYDRO-1H-PYRAZOLO[3,4-C]PYRIDIN-7-ONE COMPOUNDS AND PREPARATION THEREOF

CROSS-REFERENCE TO RELATED APPLICATIONS

This application claims priority under 35 U.S.C. §119 to Korean Patent Application No. 10-2010-0060138, filed on Jun. 24, 2010, in the Korean Intellectual Property Office, the disclosure of which is incorporated herein by reference in its entirety.

BACKGROUND (a) Technical Field

The present disclosure relates to a novel 1,6-disubstituted-4,5,6,7-tetrahydro-1H-pyrazolo[3,4-c]pyridin-7-one compound, a pharmaceutically acceptable salt compound thereof, a method for preparing the novel compound, and an anticancer pharmaceutical composition including the novel compound as an effective ingredient.

(b) Background Art

Cancer is an intractable disease whereby tumor cells grow uncontrollably, killing normal cells and metastasizing to other organs, and leading to a lot of pains and ultimately death. The factors that cause cancer are largely classified as internal and external ones. The internal factors include genetic and immunological factors, whereas the external ones include chemicals, radiation, viral infection, etc. It is still unclear through what mechanism normal cells turn into cancer cells. However, more than 80% is presumed to be caused by the external factors. Genetically, cancer is caused by the imbalance between tumor-promoting oncogenes and tumor suppressor genes results. Also classified as blood or solid cancer, the cancer occurs in nearly all parts of the body, including lungs, stomach, liver, breasts, uterus, esophagus, prostate, large intestine and skin.

Cancer treatment is performed by surgery, radiotherapy or chemotherapy. Especially, as cancer is detected earlier with the development of diagnostic techniques, the therapeutic effect by chemotherapy is improving. Nevertheless, development of anticancer agents for different mechanisms is still insufficient. Thus, use of anticancer agents is limited. Further, drug resistance remains as an important problem to be solved.

Currently known targets for anticancer agents include protein kinases (mainly PKBa (Akt1) and PKCb), Aurora kinases (ARK1, ARK2 and ARK3), cyclin-dependent kinases (mainly CDK 2), glycogen synthase kinases (mainly GSK-3β), serine/threonine kinases such as Raf kinase, Rho kinase, etc., threonine kinases, epidermal growth factor receptor (EGFR), human epidermal growth factor receptors (HER1, HER2, HER3 and HER4), stem cell factor receptor (c-Kit), rearranged during transfection receptor (RET), vascular endothelial growth factors (VEGF-1 (Flt1), VEGF-2 (KDR) and VEGF-3 (Flt4)), platelet-derived growth factor receptor (PDGFR), tyrosine kinases such as bcr-abl kinase and src kinase, or the like. Besides, carbonic anhydrases, caspases 1, 2, 3, 8 and 9, tubulin, etc. are known as targets for colon cancer.

The inventors have identified that a newly designed and synthesized compound 1,6-disubstituted-3-amino-4,5,6,7-tetrahydro-1H-pyrazolo[3,4-c]pyridin-7-one has an inhibitory action against growth of various cancer cells and thus is useful as an anticancer agent.

SUMMARY

The present disclosure is directed to providing a novel 1,6-disubstituted-3-amino-4,5,6,7-tetrahydro-1H-pyrazolo[3,4-c]pyridin-7-one compound or a pharmaceutically acceptable salt compound thereof.

The present disclosure is also directed to providing an anticancer pharmaceutical composition including the novel compound, which exhibits a strong inhibitory action against growth of various cancer cells, as an effective ingredient.

The present disclosure is also directed to providing a method for preparing the 1,6-disubstituted-3-amino-4,5,6,7-tetrahydro-1H-pyrazolo[3,4-c]pyridin-7-one compound.

The present disclosure is also directed to providing a novel intermediate compound used to synthesize the 1,6-disubstituted-3-amino-4,5,6,7-tetrahydro-1H-pyrazolo[3,4-c]pyridin-7-one compound.

In one general aspect, the present disclosure provides a 1,6-disubstituted-3-amino-4,5,6,7-tetrahydro-1H-pyrazolo[3,4-c]pyridin-7-one compound represented by Chemical Formula 1 or a pharmaceutically acceptable salt thereof, which are useful in treating cancer:

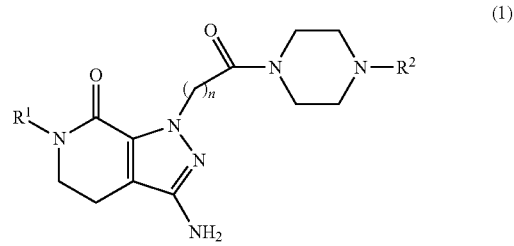

(1)

wherein n is an integer of 1, 2 or 3; $R^1$ and $R^2$, which are the same or different, are $R-(CH_2)_l-$, where R is phenyl, furyl, pyridyl or benzodioxol substituted or unsubstituted with 1 to 3 substituents selected from halo, $C_1$-$C_8$ alkyl, halo$C_1$-$C_8$ alkyl, $C_1$-$C_8$ alkoxy, amino, $C_1$-$C_8$ alkylamino and di($C_1$-$C_8$ alkyl)amino; and l is an integer of 0, 1, 2 or 3.

With superior inhibitory activity against various cancer cells, the disclosed 1,6-disubstituted-3-amino-4,5,6,7-tetrahydro-1H-pyrazolo[3,4-c]pyridin-7-one compound represented by Chemical Formula 1 or a pharmaceutically acceptable salt thereof is useful as an anticancer agent or an adjuvant thereof.

The above and other aspects and features of the invention will be discussed infra.

DETAILED DESCRIPTION

Hereinafter, reference will now be made in detail to various embodiments of the present disclosure, examples of which are illustrated in the accompanying drawings and described below. While the disclosure will be described in conjunction with exemplary embodiments, it will be understood that the present description is not intended to limit the disclosure to those exemplary embodiments. On the contrary, the disclosure is intended to cover not only the exemplary embodiments, but also various alternatives, modifications, equivalents and other embodiments, which may be included within the spirit and scope of the disclosure as defined by the appended claims.

The disclosed compound represented by Chemical Formula 1 may have a chiral center. Accordingly, the disclosed compound includes an isomer of the compound represented by Chemical Formula 1, an isomeric mixture thereof, or a racemic compound. Also, an isotopic derivative of the compound represented by Chemical Formula 1 is included in the scope of the present disclosure. The isotopic compound may be useful in biological researches.

Hereinafter, the substituents used to define the compound represented by Chemical Formula 1 according to the disclosure will be described in more detail.

The "halogen atom" may include fluorine, chlorine, bromine and iodine atoms. The "alkyl" group includes all of linear, branched and cyclic carbon chains having 1 to 8 carbon atoms. Specifically, the alkyl group may include methyl, ethyl, propyl, isopropyl, butyl, isobutyl, t-butyl, cyclopentyl, cyclohexyl, etc. The "alkoxy" group refers to an alkyl group linked to oxygen, wherein the alkyl group is as defined above. The "benzyl" group refers to a phenyl group substituted with methylene, with the methylene carbon capable of forming a covalent bond with other atoms.

Specifically, in Chemical Formula 1, $R^1$ and $R^2$, which are the same or different, may be phenyl, 3-chlorophenyl, 4-chlorophenyl, 2,3-dichlorophenyl, 2,3-difluorophenyl, 4-(trifluoromethyl)phenyl, 2-methylphenyl, 3-methylphenyl, 4-methylphenyl, 4-t-butylphenyl, 4-cyclohexylphenyl, 2,3-dimethylphenyl, 2,4-dimethylphenyl, 2,4,5-trimethylphenyl, 4-methoxyphenyl, benzyl, 4-t-butylbenzyl, 2,4,6-trimethylbenzyl, 2,3,4-trimethoxybenzyl, (benzo[d][1,3]dioxol-5-yl)methyl, furyl, furan-2-ylmethyl, or pyridin-2-yl.

The disclosure also provides a pharmaceutical composition for treating and preventing cancer comprising the 1,6-disubstituted-3-amino-4,5,6,7-tetrahydro-1H-pyrazolo[3,4-c]pyridin-7-one compound represented by Chemical Formula 1 or a pharmaceutically acceptable salt thereof as an effective ingredient.

The present disclosure further provides an anticancer agent comprising the 1,6-disubstituted-3-amino-4,5,6,7-tetrahydro-1H-pyrazolo[3,4-c]pyridin-7-one compound represented by Chemical Formula 1 or a pharmaceutically acceptable salt thereof as an effective ingredient.

Specific examples of the compound represented by Chemical Formula 1 according to the present disclosure are as follows:

3-amino-1-[{4-(2,3-dimethylphenyl)piperazin-1-yl}ethanoyl]-6-N-(p-tolyl)-4,5,6,7-tetrahydro-1H-pyrazolo[3,4-c]pyridin-7-one (Compound 1),
3-amino-1-[{4-(2,3-dimethylphenyl)piperazin-1-yl}propanoyl]-6-N-(p-tolyl)-4,5,6,7-tetrahydro-1H-pyrazolo[3,4-c]pyridin-7-one (Compound 2),
3-amino-1-{(4-phenylpiperazin-1-yl)propanoyl}-6-N-(p-tolyl)-4,5,6,7-tetrahydro-1H-pyrazolo[3,4-c]pyridin-7-one (Compound 3),
3-amino-1-[{4-(2,4-dimethylphenyl)piperazin-1-yl}propanoyl]-6-N-(p-tolyl)-4,5,6,7-tetrahydro-1H-pyrazolo[3,4-c]pyridin-7-one (Compound 4),
3-amino-1-[{4-((benzo[d][1,3]dioxol-5-yl)methyl)piperazin-1-yl}propanoyl]-6-N-(p-tolyl)-4,5,6,7-tetrahydro-1H-pyrazolo[3,4-c]pyridin-7-one (Compound 5),
3-amino-1-[{4-(2,4,6-trimethylbenzyl)piperazin-1-yl}propanoyl]-6-N-(p-tolyl)-4,5,6,7-tetrahydro-1H-pyrazolo[3,4-c]pyridin-7-one (Compound 6),
3-amino-1-[{4-(4-t-butylbenzyl)piperazin-1-yl}propanoyl]-6-N-(p-tolyl)-4,5,6,7-tetrahydro-1H-pyrazolo[3,4-c]pyridin-7-one (Compound 7),
3-amino-1-[{4-(2,3,4-trimethoxybenzyl)piperazin-1-yl}propanoyl]-6-N-(p-tolyl)-4,5,6,7-tetrahydro-1H-pyrazolo[3,4-c]pyridin-7-one (Compound 8),
3-amino-1-[{4-(4-chlorophenyl)piperazin-1-yl}propanoyl]-6-N-(p-tolyl)-4,5,6,7-tetrahydro-1H-pyrazolo[3,4-c]pyridin-7-one (Compound 9),
3-amino-1-[{4-(4-methoxyphenyl)piperazin-1-yl}propanoyl]-6-N-(p-tolyl)-4,5,6,7-tetrahydro-1H-pyrazolo[3,4-c]pyridin-7-one (Compound 10),
3-amino-1-{(N-benzyl)piperazin-1-yl}-6-N-(p-methoxyphenyl)-4,5,6,7-tetrahydro-pyrazolo[3,4-c]pyridin-7-one (Compound 11),
3-amino-1-[{4-(2,4-dimethylphenyl)piperazin-1-yl}propanoyl]-6-N-(p-methoxyphenyl)-4,5,6,7-tetrahydro-1H-pyrazolo[3,4-c]pyridin-7-one (Compound 12),
3-amino-1-[{4-(2,4,6-trimethylbenzyl)piperazin-1-yl}propanoyl]-6-N-(p-methoxyphenyl)-4,5,6,7-tetrahydro-1H-pyrazolo[3,4-c]pyridin-7-one (Compound 13),
3-amino-1-[{4-(2,3,4-trimethoxybenzyl)piperazin-1-yl}propanoyl]-6-N-(p-methoxyphenyl)-4,5,6,7-tetrahydro-1H-pyrazolo[3,4-c]pyridin-7-one (Compound 14),
3-amino-1-[{4-(2,4-dimethylphenyl)piperazin-1-yl}propanoyl]-6-N-phenyl-4,5,6,7-tetrahydro-1H-pyrazolo[3,4-c]pyridin-7-one (Compound 15),
3-amino-1-[{4-(2,4,6-trimethylbenzyl)piperazin-1-yl}propanoyl]-6-N-phenyl-4,5,6,7-tetrahydro-1H-pyrazolo[3,4-c]pyridin-7-one (Compound 16),
3-amino-1-[{4-(2,4-dimethylphenyl)piperazin-1-yl}propanoyl]-6-N-benzyl-4,5,6,7-tetrahydro-1H-pyrazolo[3,4-c]pyridin-7-one (Compound 17),
3-amino-1-{(4-phenylpiperazin-1-yl)propanoyl}-6-N-{p-(dimethylamino)phenyl}-4,5,6,7-tetrahydro-1H-pyrazolo[3,4-c]pyridin-7-one (Compound 18),
3-amino-1-[{4-(4-methoxyphenyl)piperazin-1-yl}propanoyl]-6-N-{p-(dimethylamino)phenyl}-4,5,6,7-tetrahydro-1H-pyrazolo[3,4-c]pyridin-7-one (Compound 19),
3-amino-1-{(4-phenylpiperazin-1-yl)propanoyl}-6-N-{(furan-2-yl)methyl}-4,5,6,7-tetrahydro-1H-pyrazolo[3,4-c]pyridin-7-one (Compound 20),
3-amino-1-[{4-(4-methoxyphenyl)piperazin-1-yl}propanoyl]-6-N-{(furan-2-yl)methyl}-4,5,6,7-tetrahydro-1H-pyrazolo[3,4-c]pyridin-7-one (Compound 21),
3-amino-1-{4-(2-pyridinylpiperazin-1-yl)propanoyl}-6-N-p-tolyl-4,5,6,7-tetrahydro-1H-pyrazolo[3,4-c]pyridin-7-one (Compound 22),
3-amino-1-{4-(2-pyridinylpiperazin-1-yl)propanoyl}-6-N-{(furan-2-yl)methyl}-4,5,6,7-tetrahydro-1H-pyrazolo[3,4-c]pyridin-7-one (Compound 23),
3-amino-1-[{4-(4-trifluoromethylphenyl)piperazin-1-yl}propanoyl]-6-N-(p-tolyl)-4,5,6,7-tetrahydro-1H-pyrazolo[3,4-c]pyridin-7-one (Compound 24),
3-amino-1-[{4-(2,4-dimethylphenyl)piperazin-1-yl}propanoyl]-6-N-{(furan-2-yl)methyl}-4,5,6,7-tetrahydro-1H-pyrazolo[3,4-c]pyridin-7-one (Compound 25),
3-amino-1-[{4-(2,4,5-trimethylphenyl)piperazin-1-yl}propanoyl]-6-N-(p-tolyl)-4,5,6,7-tetrahydro-1H-pyrazolo[3,4-c]pyridin-7-one (Compound 26),
3-amino-1-[{4-(4-t-butylphenyl)piperazin-1-yl}propanoyl]-6-N-(p-tolyl)-4,5,6,7-tetrahydro-1H-pyrazolo[3,4-c]pyridin-7-one (Compound 27), and
3-amino-1-[{4-(cyclohexylphenyl)piperazin-1-yl}propanoyl]-6-N-(p-tolyl)-4,5,6,7-tetrahydro-1H-pyrazolo[3,4-c]pyridin-7-one (Compound 28).

The present disclosure further provides a method for preparing the 1,6-disubstituted-3-amino-4,5,6,7-tetrahydro-1H-pyrazolo[3,4-c]pyridin-7-one compound represented by Chemical Formula 1.

As illustrated in the following Scheme 1, the 1,6-disubstituted-3-amino-4,5,6,7-tetrahydro-1H-pyrazolo[3,4-c]pyridin-7-one compound represented by Chemical Formula 1 may be prepared by alkylating a 3-amino compound represented by Chemical Formula 2 with a haloalkylcarbonyl piperazine compound represented by Chemical Formula 3.

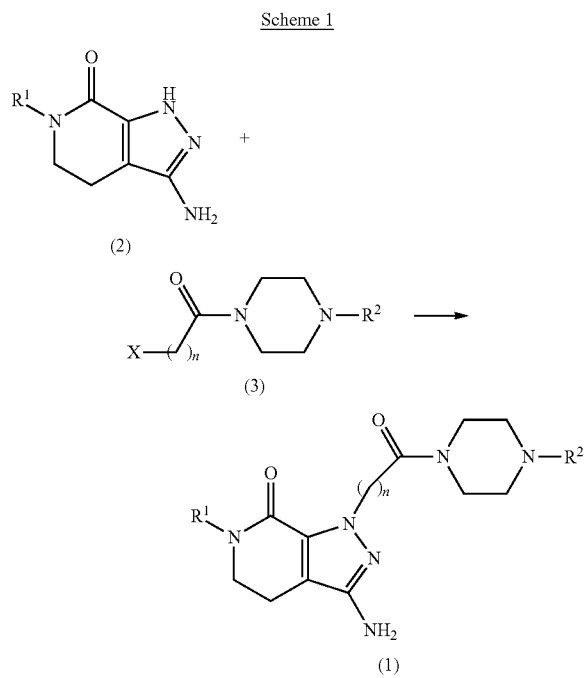

In Scheme 1, n, $R^1$ and $R^2$ are the same as defined in Chemical Formula 1 and X is a halogen atom.

The alkylation reaction may be performed under reflux in the presence of a base. The base may be a commonly used organic base selected from, for example, aliphatic alkylamines such as triethylamine and aromatic amines such as pyridine or an inorganic base selected from, for example, hydroxides, carbonates, bicarbonates, sulfates, etc. of alkali or alkaline earth metal. An inert organic solvent commonly used in the art that has no effect on the reaction may be used as a reaction solvent. The organic solvent may be, for example, an ether such as diethyl ether; a $C_1$-$C_6$ low alcohol such as methanol, ethanol or propanol; tetrahydrofuran; a halogenated compound such as chloroform, methylene chloride, etc.; a nitrile compound such as acetonitrile; or the like. In addition, a mixture solvent thereof may be used. A reaction temperature may be a reflux temperature of the solvent used, specifically from 30 to 80° C.

The 3-amino compound represented by Chemical Formula 2 used in the preparation method according to Scheme 1 is a novel intermediate compound. The present disclosure also provides the intermediate compound.

The 3-amino compound represented by Chemical Formula 2 may be prepared according Scheme 2 as follows.

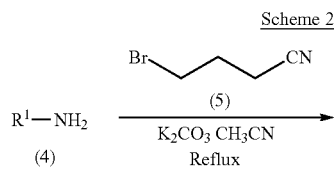

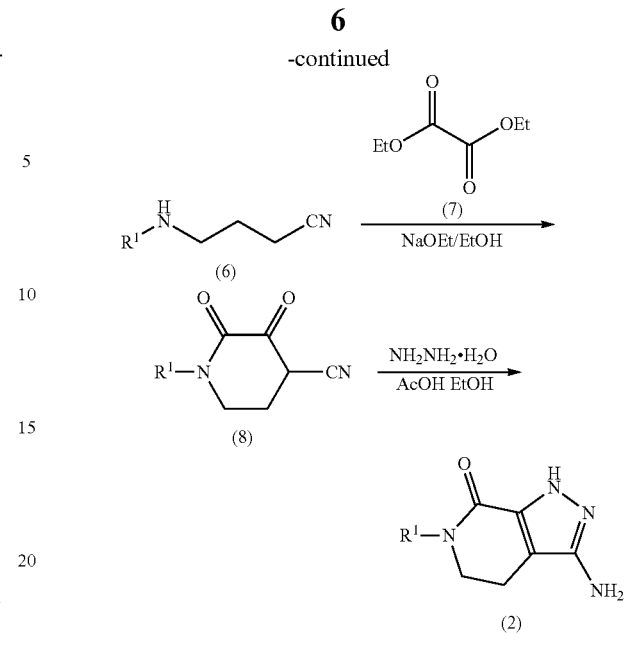

In Scheme 2, $R^1$ is the same as defined in Chemical Formula 1.

The method for preparing the 3-amino compound represented by Chemical Formula 2 according to Scheme 2 comprises:

i) reacting an amine compound represented by Chemical Formula 4 with a 4-bromobutyronitrile compound represented by Chemical Formula 5 under reflux in the presence of a base to prepare a 4-aminobutanenitrile compound represented by Chemical Formula 6;

ii) cyclizing the 4-aminobutanenitrile compound represented by Chemical Formula 6 with a β-diketone compound represented by Chemical Formula 7 by condensation the presence of a base to prepare a piperidine compound represented by Chemical Formula 8; and iii) cyclizing the piperidine compound represented by Chemical Formula 8 with hydrazine in a mixture solvent of acetic acid and alcohol to prepare the 3-amino compound represented by Chemical Formula 2.

The amine compound represented by Chemical Formula 4 which is used as a starting material in the preparation according to Scheme 2 may be commercially available or prepared according to methods disclosed in literatures. As described above, the base used in Scheme 2 may be selected from inorganic bases or organic bases commonly used in the art. An inert organic solvent commonly used in the art that has no effect on the reaction may be used as a reaction solvent. The organic solvent may be, for example, an ether such as diethyl ether; a $C_1$-$C_6$ low alcohol such as methanol, ethanol or propanol; tetrahydrofuran; a halogenated compound such as chloroform, methylene chloride, etc.; a nitrile compound such as acetonitrile; or the like. A reaction temperature may be from −30° C. to a reflux temperature of the solvent used, specifically from room temperature to 120° C., more specifically from 30 to 80° C.

The haloalkylcarbonyl piperazine compound represented by Chemical Formula 3 which is used as a starting material in the preparation according to Scheme 1 may be prepared according to Scheme 3 as follows:

Scheme 3

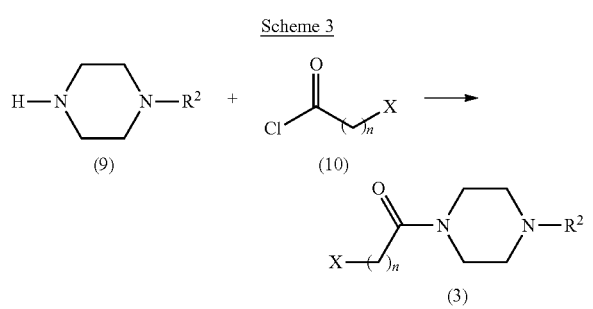

In Scheme 3, n, $R^1$, and $R^2$ are the same as defined in Chemical Formula 1 and X is a halogen atom.

According to Scheme 3, a piperazine compound represented by Chemical Formula 9 is amidated with a haloacyl halide compound represented by Chemical Formula 10 to prepare the haloalkylcarbonyl piperazine compound represented by Chemical Formula 3. The amidation reaction may be performed in the presence of an N,N-dimethylaminopyridine (DMAP) catalyst and an amine base. The amine base may be a commonly used organic base selected from, for example, aliphatic alkylamines such as triethylamine and aromatic amines such as pyridine. A commonly used organic solvent, for example, an ether such as diethyl ether; a $C_1$-$C_6$ low alcohol such as methanol, ethanol or propanol; tetrahydrofuran; a halogenated compound such as chloroform, methylene chloride, etc.; a nitrile compound such as acetonitrile; or the like may be used as a reaction solvent. In addition, a mixture solvent thereof may be used. A reaction temperature may be from −20° C. to room temperature, specifically from 0 to 20° C.

With an inhibitory effect against growth of various cancer cells, the compound represented by Chemical Formula 1 according to the disclosure may be used as an effective active ingredient of an anticancer agent. Accordingly, the present disclosure provides an anticancer agent or an anticancer pharmaceutical composition comprising the compound represented by Chemical Formula 1 or a pharmaceutically acceptable salt thereof as an effective ingredient.

The pharmaceutically acceptable salt of the compound represented by Chemical Formula 1 which is used to prepare the pharmaceutical composition according to the present disclosure may be prepared according to a method commonly known in the art. The pharmaceutically acceptable salt is not specially limited but includes, for example, salts with a nontoxic inorganic acid such as hydrochloric acid, bromic acid, sulfuric acid, phosphoric acid, nitric acid or carbonic acid; salts with a nontoxic organic acid such as formic acid, acetic acid, propionic acid, oxalic acid, succinic acid, glycolic acid, stearic acid, lactic acid, maleic acid, malonic acid, tartaric acid, citric acid, benzoic acid, p-toluenesulfonic acid, methanesulfonic acid, gluconic acid, fumaric acid, lactobionic acid, salicylic acid or acetylsalicylic acid (aspirin); salts with an amino acid such as glycine, alanine, valine, isoleucine, serine, cysteine, cystine, asparagine, glutamine, lysine, arginine, tyrosine, proline, etc.; salts with a sulfonic acid such as methanesulfonic acid, ethanesulfonic acid, benzenesulfonic acid, toluenesulfonic acid, etc.; metal salts resulting from reaction with an alkali metal such as sodium, potassium, etc.; and salts with an ammonium ion.

The pharmaceutical composition according to the present disclosure may be prepared into formulations for oral or parenteral administration common in the pharmaceutical art, for example, tablet, capsule, troche, liquid, suspension, etc., by adding a commonly used, nontoxic, pharmaceutically acceptable vehicle, adjuvant, excipient, or the like to the compound represented by Chemical Formula 1 or a pharmaceutically acceptable salt thereof in order to prevent and treat various tumors.

An excipient that may be used in the presently disclosed pharmaceutical composition may include sweetener, binder, solvent, solubilizer, wetting agent, emulsifier, isotonic agent, adsorbent, disintegrant, antioxidant, preservative, lubricant, filler, aromatic, or the like. For example, lactose, dextrose, sucrose, mannitol, sorbitol, cellulose, glycine, silica, talc, stearic acid, stearin, magnesium stearate, magnesium aluminum silicate, starch, gelatin, gum tragacanth, alginic acid, sodium alginate, methyl cellulose, sodium carboxymethyl cellulose, agar, water, ethanol, polyethylene glycol, polyvinylpyrrolidone, sodium chloride, calcium chloride, orange essence, strawberry essence, vanilla flavor, or the like may be used.

An administration dose of the compound represented by Chemical Formula 1 according to the disclosure for a human may be different depending on the patient's age, body weight, sex and health conditions, type of administration, severity of disease, or the like. A general dose for an adult patient weighing 70 kg is 0.01 to 5000 mg per day. Upon discretion of a physician or a pharmacist, the administration may be once a day or several times a day at regular time intervals.

EXAMPLES

The examples and experiments will now be described. The following examples and experiments are for illustrative purposes only and not intended to limit the scope of this disclosure.

Examples

Reference Example 1

4-(p-tolylamino)butanenitrile p-Toluidine (10.407 g, 97.116 mmol) was dissolved in anhydrous acetonitrile and, after adding potassium carbonate (49.9 g, 361.272 mmol), stirred at room temperature for 10 minutes. After slowly adding 4-bromobutyronitrile (10.1 mL, 101.972 mmol) to the resultant reaction mixture, reaction was carried out at 100° C. for 2 days. The mixture was cooled to room temperature and the produced solid was removed by filtering. The filtrate was concentrated under reduced pressure. A target compound (13.23 g, 78.2%) was yielded. A target compound was used in the next step without further purification.

$^1$H NMR (CDCl$_3$, 300 MHz) δ 7.04 (d, J=8.0 Hz, 2H), 6.57 (d, J=8.3 Hz, 2H), 3.62 (s, 1H, NH), 3.29 (q, J=6.3 Hz, 2H), 2.47 (t, J=7.0 Hz, 2H), 2.28 (s, 3H), 1.96 (t, J=6.8 Hz, 2H).

Reference Example 2

4-(4-methoxyphenylamino)butanenitrile

A target compound (5.6 g, 29.436 mmol, 77.5%) was yielded in the same manner as Reference Example 1 using p-Anisidine (4.6826 g, 38.020 mmol), potassium carbonate (19.5 g, 141.434 mmol) and 4-bromobutyronitrile (3.95 mL, 39.921 mmol).

$^1$H NMR (CDCl$_3$, 300 MHz) δ 6.81 (d, J=8.9 Hz, 2H), 6.61 (d, J=8.9 Hz, 2H), 3.77 (s, 3H), 3.42 (s, 1H, NH), 3.28 (t, J=6.6 Hz, 2H), 2.49 (t, J=7.1 Hz, 2H), 2.02-1.93 (m, 2H).

Reference Example 3

4-(benzylamino)butanenitrile

Benzylamine (5.02 mL, 46 mmol) and calcium carbonate (23.65 g, 171.12 mmol) dissolved in anhydrous acetonitrile (115 mL) were stirred for 10 minutes at room temperature. After adding 4-bromonitrile (4.78 mL, 48.3 mmol), reaction was carried out at 100° C. for 2 days. A target compound (6.69 g, 38.395 mmol, 83.5%) was yielded as liquid by separating the reaction mixture in the same manner as Reference Example 1.

$^1$H NMR (CDCl$_3$, 300 MHz) δ 7.37-7.29 (m, 5H), 3.79 (s, 2H), 2.77 (t, J=6.6 Hz, 2H), 2.48 (t, J=7.1 Hz, 2H), 1.88-1.79 (m, 2H).

Reference Example 4

2,3-dioxo-1-p-tolylpiperidine-4-carbonitrile

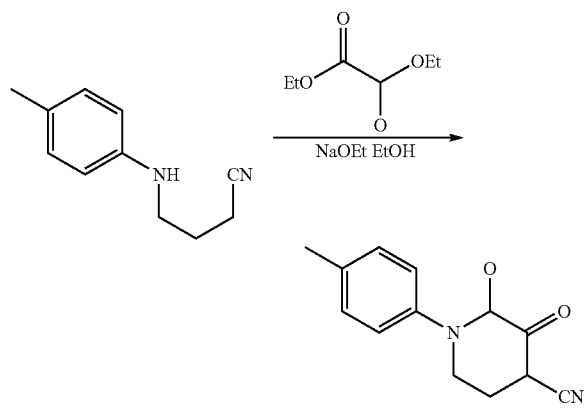

4-(p-Tolylamino)butanenitrile (13.23 g, 75.929 mmol) was dissolved in ethanol (189.8 mL). After adding diethyl oxalate (10.3 mL, 75.929 mmol) and then adding sodium ethoxide (34.0 mL, 91.115 mmol) to the resultant reaction mixture, reaction was carried out under reflux for 2 days. The reaction solution was cooled to room temperature and the concentrated solution was filtered. A target compound (8.94 g, 39.167 mmol, 51.6%) was yielded as yellow solid.

$^1$H NMR (CDCl$_3$, 300 MHz) δ 7.65 (s, 1H), 7.25 (d, J=8.5 Hz, 2H), 7.18 (d, J=8.3 Hz, 2H), 3.92 (t, J=6.9 Hz, 2H), 2.76 (t, J=6.9 Hz, 2H), 2.38 (s, 3H).

Reference Example 5

1-(4-methoxyphenyl)-2,3-dioxopiperidine-4-carbonitrile

A target compound (4.87 g, 19.938 mmol, 67.7%) was yielded as yellow solid in the same manner as Reference Example 4 using 4-(4-methoxyphenylamino)butanenitrile (5.6 g, 29.436 mmol), diethyl oxalate (4.19 mL, 30.908 mmol) and sodium ethoxide (14.3 mL, 38.267 mmol).

$^1$H NMR (DMSO, 300 MHz) δ 7.26 (d, J=8.7 Hz, 2H), 6.96 (d, J=8.7 Hz, 2H), 3.79 (t, J=6.8 Hz, 2H), 3.76 (s, 3H), 2.61 (t, J=6.7 Hz, 2H).

Reference Example 6

1-benzyl-2,3-dioxopiperidine-4-carbonitrile

A target compound 4.1 g (17.962 mmol, 46.8%) was yielded as yellow solid in the same manner as Reference Example 4 using 4-(benzylamino)butanenitrile (6.69 g, 38.395 mmol), diethyl oxalate (5.46 mL, 40.314 mmol) and sodium ethoxide (18.6 mL, 49.913 mmol).

$^1$H NMR (CDCl$_3$, 300 MHz) δ 7.84 (s, 1H), 7.41-7.31 (m, 3H), 7.30-7.25 (m, 2H), 4.65 (s, 2H), 3.42 (t, J=7.1 Hz, 2H), 2.56 (t, J=7.1 Hz, 2H).

Reference Example 7

3-amino-5,6-dihydro-6-p-tolyl-1H-pyrazolo[3,4-c]pyridin-7(4H)-one

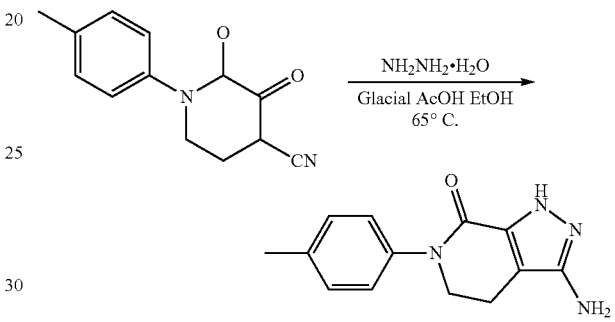

2,3-Dioxo-1-p-tolylpiperidine-4-carbonitrile (3.56 g, 15.597 mmol) was added to anhydrous ethanol (52.0 mL) and dissolved by heating to 60° C. After adding hydrazine hydrochloride (1.06 mL, 21.836 mmol) and glacial acetic acid (1.34 mL, 23.396 mmol) room temperature, reaction was carried out for 2 days. After removing ethanol by distillation, the produced solid was filtered and then acetic acid was completely removed by washing with NaHCO$_3$ twice or more times. A target compound (3.25 g, 13.414 mmol, 86.0%) was yielded as white solid.

$^1$H NMR (DMSO, 300 MHz) δ 12.24 (s, 1H, NH), 7.23-7.16 (m, 4H), 4.84 (s, 2H, NH$_2$), 3.87 (t, J=6.6 Hz, 2H), 2.69 (t, J=6.6 Hz, 2H), 2.30 (s, 3H).

Reference Example 8

3-amino-5,6-dihydro-6-(4-methoxyphenyl)-1H-pyrazolo[3,4-c]pyridin-7(4H)-one

A target compound (1.57 g, 6.079 mmol, 91.3%) was yielded as white solid in the same manner as Reference Example 7 using 1-(4-methoxyphenyl)-2,3-dioxopiperidine-4-carbonitrile (1.63 g, 6.673 mmol), hydrazine hydrate (0.45 mL, 9.342 mmol) and glacial acetic acid (0.57 mL, 10.009 mmol).

$^1$H NMR (DMSO, 300 MHz) δ 12.26 (s, 1H, NH), 7.24 (d, J=8.7 Hz, 2H), 6.94 (d, J=8.8 Hz, 2H), 4.81 (s, 2H, NH$_2$), 3.85 (t, J=6.5 Hz, 2H), 3.76 (s, 3H), 2.69 (t, J=6.6 Hz, 2H).

Reference Example 9

3-amino-6-benzyl-5,6-dihydro-1H-pyrazolo[3,4-c]pyridin-7(4H)-one

A target compound (4.23 g, 17.459 mmol, 97.2%) was yielded as white solid in the same manner as Reference Example 7 using 1-benzyl-2,3-dioxopiperidine-4-carbonitrile (4.1 g, 17.962 mmol), hydrazine hydrochloride (1.22 mL, 25.146 mmol) and glacial acetic acid (1.54 mL, 26.943 mmol).

$^1$H NMR (CDCl$_3$, 300 MHz) δ 7.38-7.27 (m, 5H), 4.74 (s, 2H), 4.69 (s, 2H, NH$_2$), 3.52 (t, J=6.8 Hz, 2H), 2.64 (t, J=6.8 Hz, 2H).

Reference Example 10

1-(4-t-butylphenyl)piperazine

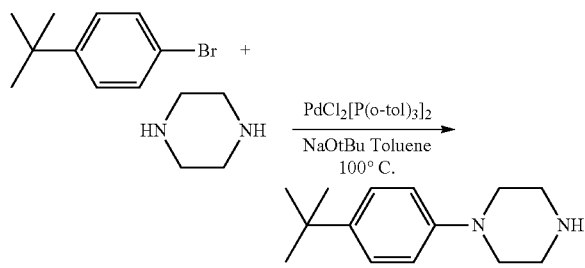

1-Bromo-4-t-butylbenzene (2.38 mL, 14 mmol), piperazine (1.8 g, 21 mmol), sodium t-butoxide (1.95 g, 20.3 mmol) and dichlorobis(tri-o-tolylphosphine)palladium(II) (330.1 mg, 0.42 mmol) were dissolved in anhydrous toluene and reacted for 3 hours while heating at 100° C. After identifying complete disappearance of 1-bromo-4-t-butylbenzene by TLC, the reaction solution was filtered with celite. The filtrate was concentrated and purified by separation through column chromatography (CH$_2$Cl$_2$/MeOH, 1:1). A target compound (1.47 g, 6.732 mmol, 48.2%) was yielded.

$^1$H NMR (CDCl$_3$, 300 MHz) δ 7.31 (d, J=8.6 Hz, 2H), 6.90 (d, J=8.6 Hz, 2H), 3.14 (br, 4H), 3.04 (br, 4H), 1.57 (s, 1H, NH), 1.31 (s, 9H).

$^{13}$C NMR (CDCl$_3$, 75 MHz) δ 149.5, 142.4, 125.8, 115.7, 50.6, 46.3, 33.9, 31.4.

Reference Example 11

1-(2,4,5-trimethylphenyl)piperazine

A target compound (1.03 g, 5.041 mmol, 40.2%) was yielded in the same manner as Reference Example 10 by reacting 5-bromo-1,2,4-trimethylbenzene (2.5 g, 12.556 mmol) with piperazine (4.32 g, 50.224 mmol), sodium t-butoxide (1.75 g, 18.206 mmol) and dichlorobis(tri-o-tolylphosphine)palladium(II) (295.5 mg, 0.37 mmol) and purifying by separation through column chromatography (CH$_2$Cl$_2$/MeOH, 1:1).

$^1$H NMR (CDCl$_3$, 300 MHz) δ 6.97 (s, 1H), 6.83 (s, 1H), 3.14 (br, 4H), 2.96 (br, 4H), 2.24 (s, 3H), 2.22 (s, 3H), 2.19 (s, 3H).

Reference Example 12

1-(4-cyclohexylphenyl)piperazine

A target compound (2.01 g, 8.224 mmol, 45.7%) was yielded in the same manner as Reference Example 10 by reacting 1-bromo-4-cyclohexylbenzene (3.34 mL, 18 mmol) with piperazine (2.01 g, 23.4 mmol), sodium t-butoxide (2.51 g, 26.1 mmol) and dichlorobis(tri-o-tolylphosphine)palladium(II) (424.4 mg, 0.54 mmol) and purifying by separation through column chromatography (CH$_2$Cl$_2$/MeOH, 1:1).

$^1$H NMR (CDCl$_3$, 300 MHz) δ 7.13 (d, J=8.5 Hz, 2H), 6.88 (d, J=8.6 Hz, 2H), 3.13-3.10 (m, 4H), 3.05-3.02 (m, 4H), 2.44 (br, 1H), 1.85 (br, 4H), 1.74 (d, J=12.1 Hz, 1H), 1.46-1.21 (m, 5H).

Reference Example 13

3-chloro-1-(4-(4-methoxyphenyl)piperazin-1-yl)propan-1-one

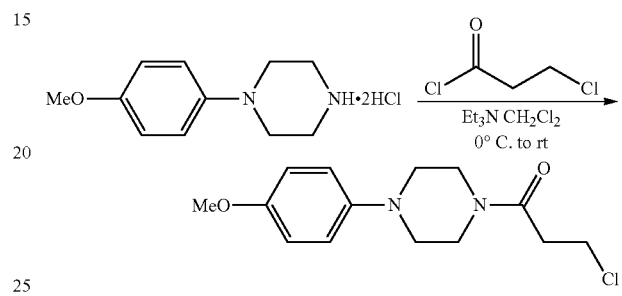

1-(4-Methoxyphenyl)piperazine dihydrochloride (1.85 g, 6.976 mmol) was dissolved in methylene chloride. After adding triethylamine (1.9 mL, 13.952 mmol) dropwise at 0° C. and then dissolving, the mixture was stirred for 30 minutes. After adding 3-chloropropionyl chloride (0.67 mL, 6.976 mmol), the reaction solution was stirred at room temperature for 1 hour. After adding methanol, the reaction solution was extracted with methylene chloride. The organic layer was dried with desiccant and then filtered. The filtrate was concentrated and purified by column chromatography (EtOAc/hexane, 4:1). A target compound (1.76 g, 6.224 mmol, 89.3%) was yielded as white solid.

$^1$H NMR (CDCl$_3$, 300 MHz) δ 6.93-6.85 (m, 4H), 3.87 (t, J=7.0 Hz, 2H), 3.80 (br, 2H), 3.79 (s, 3H), 3.64 (br, 2H), 3.06 (br, 4H), 2.86 (t, J=7.0 Hz, 2H).

Reference Example 14

3-chloro-1-(4-(4-chlorophenyl)piperazin-1-yl)propan-1-one 1-(4-Chlorophenyl)piperazine dihydrochloride (1.88 g, 6.973 mmol) was dissolved in methylene chloride and, after slowly adding triethylamine (1.9 mL, 13.946 mmol) at 0° C., stirred for 5 minutes. After adding 3-chloropropionyl chloride (0.67 mL, 6.973 mmol), the reaction solution was stirred at room temperature. After extracting with methylene chloride, the organic layer was dried with desiccant and then filtered. The filtrate was concentrated and purified by column chromatography (EtOAc/hexane, 4:1). A target compound (1.03 g, 3.586 mmol, 51.5%) was yielded as white solid.

$^1$H NMR (CDCl$_3$, 300 MHz) δ 7.24 (d, J=9.0 Hz, 2H), 6.85 (d, J=8.9 Hz, 2H), 3.87 (t, J=6.9 Hz, 2H), 3.81 (br, 2H), 3.65 (br, 2H), 3.16 (br, 4H), 2.86 (t, J=6.9 Hz, 2H).

Reference Example 15

3-chloro-1-(4-phenylpiperazin-1-yl)propan-1-one

A target compound (2.41 g, 9.535 mmol, 80.35%) was yielded as white solid in the same manner as Reference Example 13 using 1-phenylpiperazine (1.82 mL, 12 mmol) and 3-chloropropionyl chloride (0.67 mL, 6.976 mmol).

$^1$H NMR (CDCl$_3$, 300 MHz) δ 7.30 (t, J=8.1 Hz, 2H), 6.96-6.90 (m, 3H), 3.87 (t, J=7.0 Hz, 2H), 3.81 (br, 2H), 3.65 (br, 2H), 3.19 (br, 4H), 2.87 (t, J=7.0 Hz, 2H).

Reference Example 16

3-chloro-1-(4-(2,4-dimethylphenyl)piperazin-1-yl)propan-1-one

A target compound (1.72 g, 6.125 mmol, 58.3%) was yielded as white solid in the same manner as Reference Example 13 using 1-(2,4-dimethylphenyl)piperazine (2 g, 10.510 mmol) and 3-chloropropionyl chloride (1.0 mL, 10.510 mmol).

$^1$H NMR (CDCl$_3$, 300 MHz) δ 7.04 (s, 1H), 6.99 (d, J=8.0 Hz, 1H), 6.89 (d, J=8.0 Hz, 1H), 3.87 (t, J=7.0 Hz, 2H), 3.78 (t, J=4.7 Hz, 2H), 3.62 (t, J=4.9 Hz, 2H), 2.91-2.85 (m, 6H), 2.30 (s, 3H), 2.29 (s, 3H).

Reference Example 17

3-chloro-1-(4-(pyridin-2-yl)piperazin-1-yl)propan-1-one

A target compound (1.3 g, 5.123 mmol, 43.3%) was yielded as white solid in the same manner as Reference Example 13 using 1-(pyridin-2-yl)piperazine (1.8 mL, 11.822 mmol) and 3-chloropropionyl chloride (1.13 mL, 11.822 mmol).

$^1$H NMR (CDCl$_3$, 300 MHz) δ 8.21 (d, J=6.6 Hz, 1H), 7.52 (t, J=7.8 Hz, 1H), 6.71-6.65 (m, 2H), 3.87 (t, J=6.9 Hz, 2H), 3.78 (t, J=5.3 Hz, 2H), 3.66-3.59 (m, 4H), 3.52 (t, J=5.3 Hz, 2H), 2.87 (t, J=6.9 Hz, 2H).

Reference Example 18

3-chloro-1-(4-(4-(trifluoromethyl)phenyl)piperazin-1-yl)propan-1-one

A target compound (492.9 mg, 1.536 mmol, 70.7%) was yielded as white solid in the same manner as Reference Example 13 using N-(α,α,α-trifluoro-p-tolyl)piperazine (500 mg, 2.171 mmol) and 3-chloropropionyl chloride (208.8 mg, 2.171 mmol).

$^1$H NMR (CDCl$_3$, 300 MHz) δ 7.52 (d, J=8.7 Hz, 2H), 6.94 (d, J=8.6 Hz, 2H), 3.87 (t, J=6.9 Hz, 2H), 3.82 (t, J=5.2 Hz, 2H), 3.67 (t, J=5.1 Hz, 2H), 3.34-3.27 (m, 4H), 2.87 (t, J=6.9 Hz, 2H).

Reference Example 19

3-chloro-1-(4-(2,4,5-trimethylphenyl)piperazin-1-yl)propan-1-one

A target compound (925 mg, 3.137 mmol, 62.5%) was yielded as liquid in the same manner as Reference Example 13 by reacting 1-(2,4,5-trimethylphenyl)piperazine (1.03 g, 5.041 mmol) with 3-chloropropionyl chloride (484.9 mg, 5.041 mmol) and purifying by separation through column chromatography (EtOAc/hexane, 1:2).

$^1$H NMR (CDCl$_3$, 300 MHz) δ 6.98 (s, 1H), 6.77 (s, 1H), 3.87 (t, J=7.0 Hz, 2H), 3.78 (t, J=4.8 Hz, 2H), 3.61 (t, J=4.9 Hz, 2H), 2.91-2.84 (m, 6H), 2.27 (s, 3H), 2.22 (s, 3H), 2.20 (s, 3H).

Reference Example 20

1-(4-(4-t-butylphenyl)piperazin-1-yl)-3-chloropropan-1-one

A target compound (1.59 g, 5.148 mmol, 76.4%) was yielded as liquid in the same manner as Reference Example 13 by reacting 1-(4-t-butylphenyl)piperazine (1.47 g, 6.732 mmol) with 3-chloropropionyl chloride (647.5 mg, 6.732 mmol) and purifying by separation through column chromatography (EtOAc:hexane:CH$_2$Cl$_2$, 1:1:5).

$^1$H NMR (CDCl$_3$, 300 MHz) δ 7.32 (d, J=8.8 Hz, 2H), 6.89 (d, J=8.8 Hz, 2H), 3.87 (t, J=7.0 Hz, 2H), 3.80 (t, J=5.1 Hz, 2H), 3.64 (t, J=5.1 Hz, 2H), 3.19-3.13 (m, 4H), 2.87 (t, J=7.0 Hz, 2H), 1.31 (s, 9H).

Reference Example 21

3-chloro-1-(4-(4-cyclohexylphenyl)piperazin-1-yl)propan-1-one

A target compound (2.2 g, 6.569 mmol) was yielded as white solid in the same manner as Reference Example 13 by reacting 1-(4-cyclohexylphenyl)piperazine (2.01 g, 8.224 mmol) with 3-chloropropionyl chloride (0.79 mL, 8.224 mmol) and purifying by separation through column chromatography (EtOAc:hexane:CH$_2$Cl$_2$, 1:1:5).

$^1$H NMR (CDCl$_3$, 300 MHz) δ 7.14 (d, J=8.6 Hz, 2H), 6.88 (d, J=8.6 Hz, 2H), 3.86 (t, J=7.0 Hz, 2H), 3.80 (t, J=5.1 Hz, 2H), 3.64 (t, J=5.1 Hz, 2H), 3.18-3.12 (m, 4H), 2.86 (t, J=7.0 Hz, 2H), 2.45 (br, 1H), 1.84 (br, 4H), 1.75 (d, J=12.0 Hz, 1H), 1.46-1.22 (m, 5H).

Reference Example 22

1-N-t-butoxycarbonyl-3-amino-4,5,6,7-tetrahydro-6-N-(p-tolyl)pyrazolo[3,4-c]pyridin-7-one 3-Amino-5,6-dihydro-6-p-tolyl-1H-pyrazolo[3,4-c]pyridin-7(4H)-one (1 g, 4.127 mmol) synthesized in Reference Example 7 and potassium percarbonate (1.1 g, 8.254 mmol) were dissolved in anhydrous tetrahydrofuran (10.3 mL). After adding di-t-butyl dicarbonate (990.6 mg, 4.539 mmol), reaction was carried out at room temperature for 2 days. After extracting the reaction mixture with methylene chloride, the organic layer was dried with MgSO$_4$, concentrated under reduced pressure, and then purified. A target compound (987.8 mg, 2.885 mmol, 70.1%) was yielded.

$^1$H NMR (CDCl$_3$, 300 MHz) δ 7.20 (s, 4H), 5.31 (s, 2H, NH$_2$), 3.93 (t, J=6.4 Hz, 2H), 2.73 (t, J=6.4 Hz, 2H), 2.35 (s, 3H), 1.65 (s, 9H).

Reference Example 23

1-N-t-butoxycarbonyl-3-amino-4,5,6,7-tetrahydro-6-N-(4-methoxyphenyl)pyrazolo[3,4-c]pyridin-7-one A target compound was yielded in the same manner as Reference Example 22 using 3-amino-5,6-dihydro-6-(4-methoxyphenyl)-1H-pyrazolo[3,4-c]pyridin-7(4H)-one synthesized in Reference Example 8.

¹H NMR (CDCl₃, 300 MHz) δ 7.24 (d, J=8.9 Hz, 2H), 6.93 (d, J=8.9 Hz, 2H), 5.26 (s, 2H, NH₂), 3.93 (t, J=6.4 Hz, 2H), 3.82 (s, 3H), 2.74 (t, J=6.4 Hz, 2H), 1.66 (s, 9H).

Example 1

3-amino-1-[{4-(2,3-dimethylphenyl)piperazin-1-yl}ethanoyl]-6-N-(p-tolyl)-4,5,6,7-1H-pyrazolo[3,4-c]pyridin-7-one (Compound 1)

1-N-t-Butoxycarbonyl-3-amino-4,5,6,7-tetrahydro-6-N-(p-tolyl)pyrazolo[3,4-c]pyridin-7-one (120 mg, 0.350 mmol) was dissolved in anhydrous acetonitrile (1.5 mL) and, after adding potassium carbonate (53.2 mg, 0.385 mmol), stirred at room temperature for 30 minutes. After adding 2-chloro-1-{4-(2,3-dimethylphenyl)piperazin-1-yl}ethanone (97.9 mg, 0.367 mmol), the mixture solution was reacted overnight under reflux. The reaction mixture was cooled to room temperature and then extracted with methylene chloride. The organic layer was washed with water and then dried with MgSO₄. After removing the solid by filtering, the solution was concentrated under reduced pressure and purified by separation through column chromatography (MeOH/CH₂Cl₂, 1:20). A target compound (22.7 mg, 0.048 mmol, 13.7%) was yielded.
¹H NMR (CDCl₃, 300 MHz) δ 7.24-7.17 (m, 4H), 7.09 (t, J=7.6 Hz, 1H), 6.95 (d, J=7.3 Hz, 1H), 6.87 (d, J=7.8 Hz, 1H), 5.06 (s, 2H), 4.08 (s, 2H, NH₂), 3.96 (t, J=6.4 Hz, 2H), 3.80 (br, 4H), 2.89 (br, 4H), 2.77 (t, J=6.4 Hz, 2H), 2.35 (s, 3H), 2.29 (s, 3H), 2.24 (s, 3H).
¹³C NMR (CDCl₃, 75 MHz) δ 165.6, 161.3, 150.6, 142.2, 142.0, 140.3, 138.2, 136.0, 131.3, 129.5, 125.9, 125.7, 125.5, 116.8, 103.6, 52.3, 51.8, 50.5, 46.4, 42.7, 21.0, 20.6, 19.6, 13.9.

Example 2

3-amino-1-[{4-(2,3-dimethylphenyl)piperazin-1-yl}propanoyl]-6-N-(p-tolyl)-4,5,6,7-tetrahydro-1H-pyrazolo[3,4-c]pyridin-7-one (Compound 2)

A target compound (80.9 mg, 0.166 mmol, 47.5%) was yielded as white solid in the same manner as Example 1 by reacting 1-N-t-butoxycarbonyl-3-amino-4,5,6,7-tetrahydro-6-N-(p-tolyl)pyrazolo[3,4-c]pyridin-7-one (120 mg, 0.350 mmol) with potassium carbonate (53.2 mg, 0.385 mmol) and 3-chloro-1-(4-(2,3-dimethylphenyl)piperazin-1-yl)propan-1-one (103.0 mg, 0.367 mmol).
¹H NMR (CDCl₃, 300 MHz) δ 7.22-7.16 (m, 4H), 7.07 (t, J=7.7 Hz, 1H), 6.93 (d, J=7.3 Hz, 1H), 6.84 (d, J=7.9 Hz, 1H), 4.52 (s, 2H, NH₂), 4.38 (t, J=5.0 Hz, 2H), 3.91 (t, J=6.4 Hz, 2H), 3.57 (br, 4H), 3.01 (t, J=5.0 Hz, 2H), 2.81 (br, 4H), 2.72 (t, J=6.4 Hz, 2H), 2.34 (s, 3H), 2.27 (s, 3H), 2.23 (s, 3H).
¹³C NMR (CDCl₃, 75 MHz) δ 169.7, 161.6, 150.7, 142.3, 141.9, 140.4, 138.2, 135.8, 131.3, 129.5, 125.9, 125.6, 125.5, 116.7, 120.1, 52.1, 51.9, 45.9, 42.9, 42.4, 33.4, 21.0, 20.6, 19.5, 13.8.

Example 3

3-amino-1-{(4-phenylpiperazin-1-yl)propanoyl}-6-N-(p-tolyl)-4,5,6,7-tetrahydro-1H-pyrazolo[3,4-c]pyridin-7-one (Compound 3)

A target compound (77.8 mg, 0.169 mmol, 44.7%) was yielded as liquid in the same manner as Example 1 by reacting 1-N-t-butoxycarbonyl-3-amino-4,5,6,7-tetrahydro-6-N-(p-tolyl)pyrazolo[3,4-c]pyridin-7-one (130 mg, 0.379 mmol) with potassium carbonate (57.6 mg, 0.417 mmol) and 3-chloro-1-(4-phenylpiperazin-1-yl)propan-1-one (100.6 mg, 0.398 mmol).
¹H NMR (CDCl₃, 300 MHz) δ 7.25 (t, J=7.9 Hz, 2H), 7.15 (s, 4H), 6.88 (d, J=8.8 Hz, 3H), 4.53 (s, 2H, NH₂), 4.34 (t, J=5.0 Hz, 2H), 3.83 (t, J=6.4 Hz, 2H), 3.70 (br, 2H), 3.56 (br, 2H), 3.07 (br, 4H), 2.97 (t, J=5.0 Hz, 2H), 2.66 (t, J=6.4 Hz, 2H), 2.31 (s, 3H).
¹³C NMR (CDCl₃, 75 MHz) δ 169.6, 161.6, 150.7, 142.1, 142.0, 140.3, 135.9, 129.5, 129.2, 125.5, 120.6, 116.6, 102.2, 51.9, 49.4, 49.2, 45.3, 42.9, 41.8, 33.2, 21.0, 19.4.

Example 4

3-amino-1-[{4-(2,4-dimethylphenyl)piperazin-1-yl}propanoyl]-6-N-(p-tolyl)-4,5,6,7-tetrahydro-1H-pyrazolo[3,4-c]pyridin-7-one (Compound 4)

A target compound (102.8 mg, 0.211 mmol, 55.7%) was yielded as white solid in the same manner as Example 1 by reacting 1-N-t-butoxycarbonyl-3-amino-4,5,6,7-tetrahydro-6-N-(p-tolyl)pyrazolo[3,4-c]pyridin-7-one (130 mg, 0.379 mmol) with potassium carbonate (57.6 mg, 0.417 mmol) and 3-chloro-1-{4-(2,4-dimethylphenyl)piperazin-1-yl}propan-1-one (111.7 mg, 0.398 mmol).
¹H NMR (CDCl₃, 300 MHz) δ 7.21-7.15 (m, 4H), 7.01 (s, 1H), 6.96 (d, J=8.2 Hz, 1H), 6.84 (d, J=8.0 Hz, 1H), 4.56 (s, 2H, NH₂), 4.37 (t, J=4.7 Hz, 2H), 3.89 (t, J=6.4 Hz, 2H), 3.70 (br, 2H), 3.55 (br, 2H), 3.00 (t, J=4.8 Hz, 2H), 2.79 (br, 4H), 2.70 (t, J=6.4 Hz, 2H), 2.33 (s, 3H), 2.27 (s, 6H).
¹³C NMR (CDCl₃, 75 MHz) δ 169.6, 161.6, 148.2, 142.2, 142.0, 140.4, 135.8, 133.3, 132.5, 131.9, 129.5, 127.1, 125.5, 119.0, 102.1, 51.9, 51.9, 51.7, 45.9, 42.9, 42.4, 33.4, 21.0, 20.7, 19.5, 17.6.

Example 5

3-amino-1-[{4-((benzo[d][1,3]dioxol-5-yl)methyl)piperazin-1-yl}propanoyl]-6-N-(p-tolyl)-4,5,6,7-tetrahydro-1H-pyrazolo[3,4-c]pyridin-7-one (Compound 5)

A target compound (101.7 mg, 0.196 mmol, 51.9%) was yielded as white solid in the same manner as Example 1 by reacting 1-N-t-butoxycarbonyl-3-amino-4,5,6,7-tetrahydro-6-N-(p-tolyl)pyrazolo[3,4-c]pyridin-7-one (130 mg, 0.379 mmol) with potassium carbonate (57.6 mg, 0.417 mmol) and 1-[4-{(benzo[d][1,3]dioxol-5-yl)methyl}piperazin-1-yl]-3-chloropropan-1-one (123.7 mg, 0.398 mmol).
¹H NMR (CDCl₃, 300 MHz) δ 7.19-7.11 (m, 4H), 6.79 (s, 1H), 6.72-6.66 (m, 2H), 5.90 (s, 2H), 4.53 (s, 2H, NH₂), 4.29 (t, J=4.8 Hz, 2H), 3.86 (t, J=6.4 Hz, 2H), 3.53 (br, 2H), 3.38 (br, 2H), 3.36 (s, 2H), 2.90 (t, J=4.8 Hz, 2H), 2.66 (t, J=6.3 Hz, 2H), 2.32 (br, 4H), 2.29 (s, 3H).
¹³C NMR (CDCl₃, 75 MHz) δ 169.4, 161.6, 147.7, 146.7, 142.1, 142.0, 140.4, 135.8, 131.3, 129.5, 125.5, 122.1, 109.3, 107.9, 102.0, 100.9, 62.4, 52.6, 52.3, 51.9, 45.2, 42.8, 41.8, 33.3, 21.0, 19.5.

Example 6

3-amino-1-[{4-(2,4,6-trimethylbenzyl)piperazin-1-yl}propanoyl]-6-N-(p-tolyl)-4,5,6,7-tetrahydro-1-H-pyrazolo[3,4-c]pyridin-7-one (Compound 6)

A target compound (130.2 mg, 0.253 mmol, 56.7%) was yielded as yellow solid in the same manner as Example 1 by reacting 3-amino-5,6-dihydro-6-N-(p-tolyl)-1H-pyrazolo[3,4-c]pyridin-7(4H)-one (108.2 mg, 0.446 mmol) with potassium carbonate (92.4 mg, 0.669 mmol) and 1-{4-(2,4,6-trimethylbenzyl)piperazin-1-yl}-3-chloropropan-1-one (151.3 mg, 0.490 mmol).

$^1$H NMR (CDCl$_3$, 300 MHz) δ 7.22-7.14 (m, 4H), 6.83 (s, 2H), 4.56 (s, 2H, NH$_2$), 4.32 (t, J=4.8 Hz, 2H), 3.89 (t, J=6.4 Hz, 2H), 3.49 (br, 2H), 3.44 (s, 2H), 3.34 (br, 2H), 2.93 (t, J=4.9 Hz, 2H), 2.69 (t, J=6.4 Hz, 2H), 2.38 (br, 4H), 2.32 (s, 9H), 2.26 (s, 3H).

$^{13}$C NMR (CDCl$_3$, 75 MHz) δ 169.3, 161.6, 142.1, 142.0, 140.4, 138.0, 136.6, 135.8, 131.0, 129.6, 129.5, 128.9, 125.5, 125.3, 102.0, 55.6, 52.4, 52.1, 51.9, 45.6, 42.8, 42.2, 33.4, 21.0, 20.9, 20.0, 19.5.

Example 7

3-amino-1-[{4-(4-t-butylbenzyl)piperazin-1-yl}propanoyl]-6-N-(p-tolyl)-4,5,6,7-tetrahydro-1H-pyrazolo[3,4-c]pyridin-7-one (Compound 7)

A target compound (109.8 mg, 0.207 mmol, 50.4%) was yielded as yellow solid in the same manner as Example 1 by reacting 3-amino-5,6-dihydro-6-N-(p-tolyl)-1H-pyrazolo[3,4-c]pyridin-7(4H)-one (100 mg, 0.412 mmol) with potassium carbonate (85.4 mg, 0.618 mmol) and 1-{4-(4-t-butylbenzyl)piperazin-1-yl}-3-chloropropan-1-one (146.2 mg, 0.453 mmol).

$^1$H NMR (CDCl$_3$, 300 MHz) δ 7.33 (d, J=8.2 Hz, 2H), 7.22-7.14 (m, 6H), 4.54 (s, 2H, NH$_2$), 4.32 (t, J=4.8 Hz, 2H), 3.89 (t, J=6.4 Hz, 2H), 3.56 (br, 2H), 3.45 (s, 2H), 3.40 (br, 2H), 2.92 (t, J=4.8 Hz, 2H), 2.69 (t, J=6.4 Hz, 2H), 2.37 (br, 4H), 2.32 (s, 3H), 1.31 (s, 9H).

$^{13}$C NMR (CDCl$_3$, 75 MHz) δ 169.4, 161.6, 150.2, 142.2, 142.0, 140.4, 135.8, 134.3, 129.5, 128.8, 125.5, 125.2, 102.0, 62.4, 52.7, 52.5, 51.9, 45.3, 42.8, 41.8, 34.5, 33.4, 31.4, 21.0, 19.5.

Example 8

3-amino-1-[{4-(2,3,4-trimethoxybenzyl)piperazin-1-yl}propanoyl]-6-N-(p-tolyl)-4,5,6,7-tetrahydro-1H-pyrazolo[3,4-c]pyridin-7-one (Compound 8)

A target compound (158.4 mg, 0.281 mmol, 53.8%) was yielded as white solid in the same manner as Example 1 by reacting 3-amino-5,6-dihydro-6-N-(p-tolyl)-1H-pyrazolo[3,4-c]pyridin-7(4H)-one (126.8 mg, 0.523 mmol) with potassium carbonate (108.3 mg, 0.784 mmol) and 1-{4-(2,3,4-trimethoxybenzyl)piperazin-1-yl}-3-chloropropan-1-one (205.1 mg, 0.575 mmol).

$^1$H NMR (CDCl$_3$, 300 MHz) δ 7.15-7.07 (m, 4H), 6.89 (d, J=8.5 Hz, 1H), 6.57 (d, J=8.5 Hz, 1H), 4.53 (s, 2H, NH$_2$), 4.25 (t, J=4.7 Hz, 2H), 3.82 (t, J=6.9 Hz, 2H), 3.80 (s, 6H), 3.78 (s, 3H), 3.48 (br, 2H), 3.40 (s, 2H), 3.32 (br, 2H), 2.86 (t, J=4.6 Hz, 2H), 2.63 (t, J=6.4 Hz, 2H), 2.34 (br, 4H), 2.26 (s, 3H).

$^{13}$C NMR (CDCl$_3$, 75 MHz) δ 169.3, 161.6, 153.0, 152.5, 142.2, 142.0, 140.3, 135.7, 129.4, 125.5, 125.1, 123.1, 107.0, 102.0, 61.1, 60.7, 56.2, 55.9, 52.6, 52.3, 51.9, 45.3, 42.8, 41.8, 33.2, 20.9, 19.4.

Example 9

3-amino-1-[{4-(4-chlorophenyl)piperazin-1-yl}propanoyl]-6-N-(p-tolyl)-4,5,6,7-tetrahydro-1-H-pyrazolo[3,4-c]pyridin-7-one (Compound 9)

A target compound (117.9 mg, 0.239 mmol, 57.5%) was yielded as white solid in the same manner as Example 1 by reacting 3-amino-5,6-dihydro-6-N-(p-tolyl)-1H-pyrazolo[3,4-c]pyridin-7(4H)-one (101 mg, 0.416 mmol) with potassium carbonate (86.2 mg, 0.624 mmol) and 3-chloro-1-{4-(4-chlorophenyl)piperazin-1-yl}propan-1-one (131.2 mg, 0.457 mmol).

$^1$H NMR (CDCl$_3$, 300 MHz) δ 7.18 (d, J=8.8 Hz, 2H), 7.14 (s, 4H), 6.78 (d, J=8.8 Hz, 2H), 4.47 (s, 2H, NH$_2$), 4.34 (t, J=4.8 Hz, 2H), 3.83 (t, J=6.3 Hz, 2H), 3.68 (br, 2H), 3.53 (br, 2H), 3.02 (br, 4H), 2.97 (t, J=4.8 Hz, 2H), 2.66 (t, J=6.3 Hz, 2H), 2.30 (s, 3H).

$^{13}$C NMR (CDCl$_3$, 75 MHz) δ 169.6, 161.5, 149.4, 142.2, 141.9, 140.4, 135.8, 129.5, 129.1, 125.5, 125.3, 117.7, 102.2, 51.9, 49.3, 49.1, 45.1, 42.9, 41.6, 33.2, 21.0, 19.5.

Example 10

3-amino-1-[{4-(4-methoxyphenyl)piperazin-1-yl}propanoyl]-6-N-(p-tolyl)-4,5,6,7-tetrahydro-1H-pyrazolo[3,4-c]pyridin-7-one (Compound 10)

A target compound (154.9 mg, 0.317 mmol, 76.9%) was yielded as white solid the same manner as in Example 1 by reacting 3-amino-5,6-dihydro-6-N-(p-tolyl)-1H-pyrazolo[3,4-c]pyridin-7(4H)-one (100 mg, 0.412 mmol) with potassium carbonate (85.4 mg, 0.618 mmol) and 3-chloro-1-{4-(4-methoxyphenyl)piperazin-1-yl}propan-1-one (128.1 mg, 0.453 mmol).

$^1$H NMR (CDCl$_3$, 300 MHz) δ 7.17-7.10 (m, 4H), 6.85-6.78 (m, 4H), 4.50 (s, 2H, NH$_2$), 4.33 (t, J=4.5 Hz, 2H), 3.82 (t, J=6.4 Hz, 2H), 3.72 (s, 3H), 3.68 (br, 2H), 3.52 (br, 2H), 2.94 (br, 6H), 2.64 (t, J=6.3 Hz, 2H), 2.29 (s, 3H).

$^{13}$C NMR (CDCl$_3$, 75 MHz) δ 169.5, 161.6, 154.3, 145.0, 142.2, 141.9, 140.4, 135.7, 129.4, 125.5, 118.8, 114.5, 102.1, 55.5, 51.9, 50.9, 50.7, 45.4, 42.9, 41.9, 33.2, 21.0, 19.4.

Example 11

3-amino-1-{(N-benzyl)piperazin-1-yl}-6-N-(p-methoxyphenyl)-4,5,6,7-tetrahydro-pyrazolo[3,4-c]pyridin-7-one (Compound 11)

A target compound (20 mg, 0.047 mmol, 9.9%) was yielded as white solid in the same manner as Example 1 by reacting 1-N-t-butoxycarbonyl-3-amido-4,5,6,7-tetrahydro-6-N-(4-methoxyphenyl)pyrazolo[3,4-c]pyridin-7-one (173 mg, 0.482 mmol) with potassium carbonate (73.2 mg, 0.530 mmol) and 1-{(N-benzyl)piperazin-1-yl}-3-chloropropan-1-one (100 mg, 0.506 mmol).

$^1$H NMR (CDCl$_3$, 300 MHz) δ 7.33-7.25 (m, 3H), 7.21 (d, J=7.7 Hz, 2H), 7.10 (d, J=8.7 Hz, 2H), 6.91 (d, J=8.7 Hz, 2H), 4.68 (t, J=6.5 Hz, 2H), 4.42 (d, J=5.6 Hz, 2H), 3.90 (t, J=6.6 Hz, 2H), 3.82 (s, 3H), 3.57 (s, 2H, NH$_2$), 2.84 (t, J=6.5 Hz, 2H), 2.74 (t, J=6.6 Hz, 2H).

$^{13}$C NMR (CDCl$_3$, 75 MHz) δ 170.2, 159.1, 158.1, 148.8, 138.4, 134.6, 131.4, 128.5, 127.7, 127.2, 126.9, 114.3, 107.5, 55.5, 51.9, 46.2, 43.4, 37.5, 19.4.

Example 12

3-amino-1-[{4-(2,4-dimethylphenyl)piperazin-1-yl}propanoyl]-6-N-(p-methoxyphenyl)-4,5,6,7-tetrahydro-1H-pyrazolo[3,4-c]pyridin-7-one (Compound 12)

A target compound (70.2 mg, 0.139 mmol, 31.0%) was yielded as white solid in the same manner as Example 1 by reacting t-butyl 3-amino-4,5,6,7-tetrahydro-6-N-(4-methoxyphenyl)-7-oxopyrazolo[3,4-c]pyridin-1-carboxyl ester (161.3 mg, 0.45 mmol) with potassium carbonate (68.4 mg, 0.495 mmol) and 3-chloro-1-{4-(2,4-dimethylphenyl)piperazin-1-yl}propan-1-one (132.5 mg, 0.472 mmol).

$^1$H NMR (CDCl$_3$, 300 MHz) δ 7.21 (d, J=8.7 Hz, 2H), 7.00 (s, 1H), 6.95 (d, J=8.2 Hz, 1H), 6.88 (d, J=8.7 Hz, 2H), 6.84 (d, J=8.1 Hz, 1H), 4.56 (s, 2H, NH$_2$), 4.36 (t, J=4.7 Hz, 2H), 3.87 (t, J=6.3 Hz, 2H), 3.78 (s, 3H), 3.69 (br, 2H), 3.54 (br, 2H), 2.99 (t, J=4.7 Hz, 2H), 2.78 (br, 4H), 2.70 (t, J=6.3 Hz, 2H) 2.26 (s, 6H).

$^{13}$C NMR (CDCl$_3$, 75 MHz) δ 169.6, 161.8, 157.7, 148.2, 142.2, 142.0, 135.9, 133.0, 132.5, 131.9, 127.1, 127.0, 119.0, 114.2, 102.0, 55.4, 52.2, 51.9, 51.7, 45.9, 42.8, 42.4, 33.4, 20.7, 19.5, 17.6.

Example 13

3-amino-1-[{4-(2,4,6-trimethylbenzyl)piperazin-1-yl}propanoyl]-6-N-(p-methoxyphenyl)-4,5,6,7-tetrahydro-1H-pyrazolo[3,4-c]pyridin-7-one (Compound 13)

A target compound (81.2 mg, 0.153 mmol, 32.9%) was yielded as white solid in the same manner as Example 1 by reacting 3-amino-5,6-dihydro-6-N-(4-methoxyphenyl)-1H-pyrazolo[3,4-c]pyridin-7(4H)-one (120 mg, 0.464 mmol) with potassium carbonate (96.2 mg, 0.696 mmol) and 1-{4-(2,4,6-trimethylbenzyl)piperazin-1-yl}-3-chloropropan-1-one (157.5 mg, 0.510 mmol).

$^1$H NMR (CDCl$_3$, 300 MHz) δ 7.23 (d, J=8.7 Hz, 2H), 6.88 (d, J=8.7 Hz, 2H), 6.83 (s, 2H), 4.54 (s, 2H, NH$_2$), 4.32 (t, J=4.7 Hz, 2H), 3.87 (t, J=6.3 Hz, 2H), 3.78 (s, 3H), 3.49 (br, 2H), 3.44 (s, 2H), 3.33 (br, 2H), 2.93 (t, J=4.9 Hz, 2H), 2.69 (t, J=6.2 Hz, 2H), 2.38 (br, 4H), 2.32 (s, 6H), 2.25 (s, 3H).

$^{13}$C NMR (CDCl$_3$, 75 MHz) δ 169.3, 161.7, 157.7, 142.2, 141.9, 138.0, 136.6, 135.9, 131.0, 128.9, 126.9, 126.8, 114.3, 114.2, 101.9, 55.6, 55.4, 52.4, 52.2, 52.1, 45.5, 42.7, 42.1, 33.4, 20.9, 20.0, 19.5.

Example 14

3-amino-1-[{4-(2,3,4-trimethoxybenzyl)piperazin-1-yl}propanoyl]-6-N-(p-methoxyphenyl)-4,5,6,7-tetrahydro-1H-pyrazolo[3,4-c]pyridin-7-one (Compound 14)

A target compound (136.1 mg, 0.235 mmol, 46.8%) was yielded as white solid in the same manner as Example 1 by reacting 3-amino-5,6-dihydro-6-N-(4-methoxyphenyl)-1H-pyrazolo[3,4-c]pyridin-7(4H)-one (129.8 mg, 0.502 mmol) with potassium carbonate (104.0 mg, 0.753 mmol) and 1-{4-(2,3,4-trimethoxybenzyl)piperazin-1-yl}-3-chloropropan-1-one (196.9 mg, 0.552 mmol).

$^1$H NMR (CDCl$_3$, 300 MHz) δ 7.18 (d, J=8.8 Hz, 2H), 6.91 (d, J=8.5 Hz, 1H), 6.84 (d, J=8.8 Hz, 2H), 6.59 (d, J=8.5 Hz, 1H), 4.51 (s, 2H, NH$_2$), 4.28 (t, J=4.5 Hz, 2H), 3.85 (br, 2H), 3.82 (s, 6H), 3.80 (s, 3H), 3.73 (s, 3H), 3.51 (br, 2H), 3.42 (s, 2H), 3.36 (br, 2H), 2.89 (t, J=4.5 Hz, 2H), 2.65 (t, J=6.3 Hz, 2H), 2.36 (br, 4H).

$^{13}$C NMR (CDCl$_3$, 75 MHz) δ 169.3, 161.7, 157.6, 153.0, 152.5, 142.2, 142.1, 141.9, 135.9, 126.9, 125.0, 123.2, 114.2, 107.0, 101.9, 61.1, 60.7, 56.3, 55.9, 55.4, 52.6, 52.3, 52.1, 45.3, 42.8, 41.9, 33.3, 19.4.

Example 15

3-amino-1-[{4-(2,4-dimethylphenyl)piperazin-1-yl}propanoyl]-6-N-phenyl-4,5,6,7-tetrahydro-pyrazolo[3,4-c]pyridin-7-one (Compound 15)

A target compound (152 mg, 0.321 mmol, 61.2%) was yielded in the same manner as Example 1 by reacting 3-amino-5,6-dihydro-6-phenyl-1H-pyrazolo[3,4-c]pyridin-7(4H)-one (120 mg, 0.525 mmol) with potassium carbonate (108.7 mg, 0.787 mmol) and 3-chloro-1-{4-(2,4-dimethylphenyl)piperazin-1-yl}propan-1-one (162 mg, 0.577 mmol).

$^1$H NMR (CDCl$_3$, 300 MHz) δ 7.38-7.27 (m, 4H), 7.19 (t, J=6.7 Hz, 1H), 7.01 (s, 1H), 6.95 (d, J=8.0 Hz, 1H), 6.84 (d, J=8.0 Hz, 1H), 4.58 (s, 2H, NH$_2$), 4.37 (t, J=4.5 Hz, 2H), 3.91 (t, J=6.3 Hz, 2H), 3.69 (br, 2H), 3.53 (br, 2H), 2.99 (t, J=4.5 Hz, 2H), 2.78 (br, 4H), 2.70 (t, J=6.3 Hz, 2H), 2.26 (s, 6H).

$^{13}$C NMR (CDCl$_3$, 75 MHz) δ 169.6, 161.6, 148.2, 143.0, 142.2, 142.1, 133.3, 132.5, 131.9, 128.8, 127.1, 126.0, 125.7, 119.0, 102.1, 51.9, 51.7, 45.9, 42.9, 42.4, 33.4, 20.7, 19.5, 17.6.

Example 16

3-amino-1-[{4-(2,4,6-trimethylbenzyl)piperazin-1-yl}propanoyl]-6-N-phenyl-4,5,6,7-tetrahydropyrazolo[3,4-c]pyridin-7-one (Compound 16)

A target compound (92.7 mg, 0.185 mmol, 35.3%) was yielded in the same manner as Example 1 by reacting 3-amino-5,6-dihydro-6-phenyl-1H-pyrazolo[3,4-c]pyridin-7(4H)-one (120 mg, 0.525 mmol) with potassium carbonate (108.7 mg, 0.787 mmol) and 3-chloro-1-{4-(2,4,6-trimethylbenzyl)piperazin-1-yl}propan-1-one (178.2 mg, 0.577 mmol).

$^1$H NMR (CDCl$_3$, 300 MHz) δ 7.39-7.31 (m, 4H), 7.20 (t, J=6.6 Hz, 1H), 6.84 (s, 2H), 4.56 (s, 2H, NH$_2$), 4.34 (t, J=4.7 Hz, 2H), 3.93 (t, J=6.3 Hz, 2H), 3.50 (br, 2H), 3.44 (s, 2H), 3.34 (br, 2H), 2.94 (t, J=4.7 Hz, 2H), 2.71 (t, J=6.3 Hz, 2H), 2.38 (br, 4H), 2.32 (s, 6H), 2.26 (s, 3H).

$^{13}$C NMR (CDCl$_3$, 75 MHz) δ 169.3, 161.6, 143.0, 142.1, 142.0, 138.0, 136.6, 131.0, 129.0, 128.9, 126.0, 125.6, 125.5, 102.0, 55.6, 52.4, 52.1, 51.9, 45.5, 42.8, 42.2, 33.4, 20.9, 20.0, 19.5.

Example 17

3-amino-1-[{4-(2,4-dimethylphenyl)piperazin-1-yl}propanoyl]-6-N-benzyl-4,5,6,7-tetrahydro-1H-pyrazolo[3,4-c]pyridin-7-one (Compound 17)

Potassium carbonate (68.2 mg, 0.494 mmol) was added to a solution of t-butyl-3-amino-6-benzyl-4,5,6,7-tetrahydro-7-oxapyrazolo[3,4-c]pyridin-1-carboxylate (154 mg, 0.449 mmol) dissolved in anhydrous acetonitrile (1.9 mL) and then stirred at room temperature for 30 minutes. After adding 3-chloro-1-{4-(2,4-dimethylphenyl)piperazin-1-yl}propan-1-one (132.2 mg, 0.471 mmol), reaction was carried out overnight. A target compound (25.4 mg, 0.052 mmol, 11.6%) was yielded as white solid.

$^1$H NMR (CDCl$_3$, 300 MHz) δ 7.32-7.27 (m, 5H), 7.02 (s, 1H), 6.95 (br, 1H), 6.85 (d, J=8.0 Hz, 1H), 4.75 (s, 2H), 4.45 (s, 2H, NH$_2$), 4.36 (t, J=5.0 Hz, 2H), 3.69 (t, J=4.5 Hz, 2H), 3.56 (t, J=4.7 Hz, 2H), 3.43 (t, J=6.6 Hz, 2H), 3.01 (t, J=4.9 Hz, 2H), 2.84-2.77 (m, 4H), 2.55 (t, J=6.6 Hz, 2H), 2.27 (s, 6H).

$^{13}$C NMR (CDCl$_3$, 75 MHz) δ 169.6, 162.1, 148.2, 141.9, 141.8, 137.7, 133.3, 132.6, 131.9, 128.5, 128.2, 128.1, 127.3, 127.1, 119.0, 101.5, 51.9, 51.7, 49.4, 47.3, 45.9, 42.7, 42.4, 33.4, 20.7, 18.9, 17.6.

Example 18

3-amino-1-{(4-phenylpiperazin-1-yl)propanoyl}-6-N-{p-(dimethylamino)phenyl}-4,5,6,7-tetrahydro-1H-pyrazolo[3,4-c]pyridin-7-one (Compound 18)

A target compound (15.4 mg, 0.031 mmol, 7.8%) was yielded as solid in the same manner as Example 1 by reacting 3-amino-6-N-(4-(dimethylamino)phenyl)-5,6-dihydro-1H-pyrazolo[3,4-c]pyridin-7(4H)-one (110 mg, 0.405 mmol) with potassium carbonate (83.9 mg, 0.607 mmol) and 3-chloro-1-(4-phenylpiperazin-1-yl)propan-1-one (112.4 mg, 0.445 mmol).

$^1$H NMR (CDCl$_3$, 300 MHz) δ 7.29 (t, J=7.8 Hz, 2H), 7.17 (d, J=8.8 Hz, 2H), 6.93-6.90 (m, 3H), 6.73 (d, J=8.8 Hz, 2H), 4.46 (s, 2H, NH$_2$), 4.38 (t, J=4.8 Hz, 2H), 3.86 (t, J=6.4 Hz, 2H), 3.74 (br, 2H), 3.59 (br, 2H), 3.12 (br, 4H), 3.02 (t, J=4.8 Hz, 2H), 2.94 (s, 6H), 2.70 (t, J=6.4 Hz, 2H).

$^{13}$C NMR (CDCl$_3$, 75 MHz) δ 169.7, 161.7, 150.7, 149.1, 142.5, 141.7, 132.3, 129.3, 126.5, 120.7, 116.7, 112.9, 102.0, 52.2, 49.4, 49.3, 45.3, 42.7, 41.8, 40.8, 33.4, 19.5.

Example 19

3-amino-1-[{4-(4-methoxyphenyl)piperazin-1-yl}propanoyl]-6-N-{p-(dimethylamino)phenyl}-4,5,6,7-tetrahydro-1H-pyrazolo[3,4-c]pyridin-7-one (Compound 19)

A target compound (22.2 mg, 0.043 mmol, 11.1%) was yielded in the same manner as Example 1 by reacting 3-amino-6-N-(4-(dimethylamino)phenyl)-5,6-dihydro-1H-pyrazolo[3,4-c]pyridin-7(4H)-one (105 mg, 0.387 mmol) with potassium carbonate (80.1 mg, 0.580 mmol) and 3-chloro-1-{4-(4-methoxyphenyl)piperazin-1-yl}propan-1-one (120.1 mg, 0.425 mmol).

$^1$H NMR (CDCl$_3$, 300 MHz) δ 7.16 (d, J=8.9 Hz, 2H), 6.90-6.82 (m, 4H), 6.72 (d, J=8.9 Hz, 2H), 4.43 (s, 2H, NH$_2$), 4.38 (t, J=4.9 Hz, 2H), 3.86 (t, J=6.4 Hz, 2H), 3.77 (s, 3H), 3.73 (br, 2H), 3.58 (br, 2H), 3.00 (br, 6H), 2.93 (s, 6H), 2.69 (t, J=6.4 Hz, 2H).

$^{13}$C NMR (CDCl$_3$, 75 MHz) δ 169.6, 161.7, 154.4, 149.0, 145.0, 142.5, 141.6, 132.4, 126.5, 118.9, 114.5, 112.9, 102.0, 55.5, 52.2, 50.9, 50.8, 45.5, 42.8, 41.9, 40.8, 33.3, 19.5.

Example 20

3-amino-1-{(4-phenylpiperazin-1-yl)propanoyl}-6-N-{(furan-2-yl)methyl}-4,5,6,7-tetrahydro-1H-pyrazolo[3,4-c]pyridin-7-one (Compound 20)

A target compound (192.8 mg, 0.429 mmol, 96.2%) was yielded as solid in the same manner as Example 1 by reacting 3-amino-6-N-((furan-2-yl)methyl)-5,6-dihydro-1H-pyrazolo[3,4-c]pyridin-7(4H)-one (104 mg, 0.447 mmol) with potassium carbonate (92.6 mg, 0.670 mmol) and 3-chloro-1-(4-phenylpiperazin-1-yl)propan-1-one (124.1 mg, 0.491 mmol).

$^1$H NMR (CDCl$_3$, 300 MHz) δ 7.30-7.23 (m, 3H), 6.91-6.86 (m, 3H), 6.29-6.25 (m, 2H), 4.68 (s, 2H), 4.41 (s, 2H, NH$_2$), 4.33 (t, J=4.9 Hz, 2H), 3.69 (br, 2H), 3.26 (br, 2H), 3.48 (t, J=6.5 Hz, 2H), 3.08 (br, 4H), 2.97 (t, J=4.9 Hz, 2H), 2.54 (t, J=6.5 Hz, 2H).

$^{13}$C NMR (CDCl$_3$, 75 MHz) δ 169.5, 161.8, 151.1, 150.7, 142.0, 141.9, 141.6, 129.2, 120.5, 116.5, 110.3, 108.1, 101.8, 49.3, 49.1, 47.7, 45.2, 42.8, 42.3, 41.7, 33.1, 18.7.

Example 21

3-amino-1-[{4-(4-methoxyphenyl)piperazin-1-yl}propanoyl]-6-N-{(furan-2-yl)methyl}-4,5,6,7-tetrahydropyrazolo[3,4-c]pyridin-7-one (Compound 21)

A target compound (191.5 mg, 0.400 mmol, 93.1%) was yielded as solid in the same manner as Example 1 by reacting 3-amino-6-N-((furan-2-yl)methyl)-5,6-dihydro-1H-pyrazolo[3,4-c]pyridin-7(4H)-one (100 mg, 0.430 mmol) with potassium carbonate (89.1 mg, 0.645 mmol) and 3-chloro-1-{4-(4-methoxyphenyl)piperazin-1-yl}propan-1-one (133.7 mg, 0.473 mmol).

$^1$H NMR (CDCl$_3$, 300 MHz) δ 7.23 (s, 1H), 6.79-6.72 (m, 4H), 6.21-6.17 (m, 2H), 4.60 (s, 2H), 4.48 (s, 2H, NH$_2$), 4.25 (t, J=4.7 Hz, 2H), 3.67 (s, 3H), 3.61 (br, 2H), 3.46 (br, 2H), 3.40 (t, J=6.6 Hz, 2H), 2.88 (br, 6H), 2.48 (t, J=6.5 Hz, 2H).

$^{13}$C NMR (CDCl$_3$, 75 MHz) δ 169.4, 161.8, 154.3, 151.1, 145.0, 142.0, 141.9, 141.6, 118.8, 114.4, 110.3, 108.1, 101.7, 55.4, 50.8, 50.6, 47.6, 45.3, 42.8, 42.3, 41.8, 33.2, 18.8.

Example 22

3-amino-1-{-4-(2-pyridinylpiperazin-1-yl)propanoyl}-6-N-p-tolyl-4,5,6,7-tetrahydro-1H-pyrazolo[3,4-c]pyridin-7-one (Compound 22)

A target compound (159.6 mg, 0.347 mmol, 80.2%) was yielded as solid in the same manner as Example 1 by reacting 3-amino-5,6-dihydro-6-N-(p-tolyl)-pyrazolo[3,4-c]pyridin-7(4H)-one (105 mg, 0.433 mmol) with potassium carbonate (89.7 mg, 0.649 mmol) and 3-chloro-1-{4-(pyridin-2-yl)piperazin-1-yl}propan-1-one (120.7 mg, 0.476 mmol).

$^1$H NMR (CDCl$_3$, 300 MHz) δ 8.11 (d, J=3.3 Hz, 1H), 7.41 (t, J=7.8 Hz, 1H), 7.13-7.06 (m, 4H), 6.61-6.54 (m, 2H), 4.51 (s, 2H, NH$_2$), 4.30 (t, J=4.8 Hz, 2H), 3.78 (t, J=6.4 Hz, 2H), 3.62 (t, J=4.7 Hz, 2H), 3.44 (br, 6H), 2.92 (t, J=4.8 Hz, 2H), 2.61 (t, J=6.4 Hz, 2H), 2.25 (s, 3H).

$^{13}$C NMR (CDCl$_3$, 75 MHz) δ 169.7, 161.6, 158.8, 147.9, 142.1, 142.0, 140.4, 137.6, 135.7, 129.4, 125.5, 113.9, 107.2, 102.1, 51.9, 44.9, 44.8, 44.7, 42.8, 41.4, 33.3, 20.9, 19.4.

Example 23

3-amino-1-{4-(2-pyridinylpiperazin-1-yl)propanoyl}-6-N-{(furan-2-yl)methyl}-4,5,6,7-tetrahydro-1H-pyrazolo[3,4-c]pyridin-7-one (Compound 23)

A target compound (191.6 mg, 0.426 mmol, 96.2%) was yielded as solid in the same manner as Example 1 by reacting 3-amino-6-N-((furan-2-yl)methyl)-5,6-dihydro-1H-pyrazolo[3,4-c]pyridin-7(4H)-one (103 mg, 0.443 mmol) with potassium carbonate (91.7 mg, 0.664 mmol) and 3-chloro-1-{4-(pyridin-2-yl)piperazin-1-yl}propan-1-one (123.5 mg, 0.487 mmol).

$^1$H NMR (CDCl$_3$, 300 MHz) δ 8.07 (d, J=6.0 Hz, 1H), 7.39 (t, J=7.8 Hz, 1H), 7.21 (s, 1H), 6.57-6.51 (m, 2H), 6.19-6.15 (m, 2H), 4.59 (s, 2H), 4.46 (s, 2H, NH$_2$), 4.24 (t, J=4.9 Hz,

2H), 3.57 (t, J=5.0 Hz, 2H), 3.42-3.34 (m, 8H), 2.88 (t, J=4.9 Hz, 2H), 2.46 (t, J=6.5 Hz, 2H).

$^{13}$C NMR (CDCl$_3$, 75 MHz) δ 169.6, 161.8, 158.7, 151.1, 147.8, 142.0, 141.9, 141.7, 137.6, 113.9, 110.3, 108.1, 107.1, 101.7, 47.6, 44.9, 44.8, 44.7, 42.7, 42.2, 41.4, 33.3, 18.8.

Example 24

3-amino-1-[{4-(4-trifluoromethylphenyl)piperazin-1-yl}propanoyl]-6-N-(p-tolyl)-4,5,6,7-tetrahydro-1H-pyrazolo[3,4-c]pyridin-7-one (Compound 24)

A target compound (176.3 mg, 0.334 mmol, 85.4%) was yielded as solid in the same manner as Example 1 by reacting 3-amino-5,6-dihydro-6-N-(p-tolyl)-1H-pyrazolo[3,4-c]pyridin-7(4H)-one (95 mg, 0.392 mmol) with potassium carbonate (81.2 mg, 0.588 mmol) and 3-chloro-1-[4-{4-(trifluoromethyl)phenyl}piperazin-1-yl]propan-1-one (138.2 mg, 0.431 mmol).

$^1$H NMR (CDCl$_3$, 300 MHz) δ 7.48 (d, J=8.6 Hz, 2H), 7.15 (s, 4H), 6.89 (d, J=8.6 Hz, 2H), 4.43 (s, 2H, NH$_2$), 4.37 (t, J=5.0 Hz, 2H), 3.86 (t, J=6.4 Hz, 2H), 3.72 (t, J=4.9 Hz, 2H), 3.58 (t, J=4.9 Hz, 2H), 3.20 (br, 4H), 3.00 (t, J=5.0 Hz, 2H), 2.68 (t, J=6.4 Hz, 2H), 2.32 (s, 3H).

$^{13}$C NMR (CDCl$_3$, 75 MHz) δ 169.7, 161.5, 152.7, 142.3, 141.8, 140.4, 135.8, 129.5, 126.5, 126.4, 125.5, 114.9, 120.2, 51.9, 48.0, 47.9, 44.9, 42.8, 41.4, 33.2, 20.9, 19.5.

Example 25

3-amino-1-[{4-(2,4-dimethylphenyl)piperazin-1-yl}propanoyl]-6-N-{(furan-2-yl)methyl}-4,5,6,7-tetrahydro-1H-pyrazolo[3,4-c]pyridin-7-one (Compound 25)

A target compound (187.7 mg, 0.393 mmol, 93.3%) was yielded as solid in the same manner as Example 1 by reacting 3-amino-6-N-((furan-2-yl)methyl)-5,6-dihydro-1H-pyrazolo[3,4-c]pyridin-7(4H)-one (98 mg, 0.422 mmol) with potassium carbonate (87.4 mg, 0.633 mmol) and 3-chloro-1-{4-(2,4-dimethylphenyl)piperazin-1-yl}propan-1-one (130.2 mg, 0.464 mmol).

$^1$H NMR (CDCl$_3$, 300 MHz) δ 7.33 (s, 1H), 7.01 (s, 1H), 6.97 (d, J=8.0 Hz, 1H), 6.85 (d, J=8.0 Hz, 1H), 6.32-6.28 (m, 2H), 4.73 (s, 2H), 4.42 (s, 2H, NH$_2$), 4.35 (t, J=5.0 Hz, 2H), 3.69 (t, J=4.5 Hz, 2H), 3.56-3.49 (m, 4H), 2.99 (t, J=5.0 Hz, 2H), 2.83-2.77 (m, 4H), 2.59 (t, J=6.6 Hz, 2H), 2.27 (s, 6H).

$^{13}$C NMR (CDCl$_3$, 75 MHz) δ 169.5, 161.9, 151.2, 148.2, 142.0, 141.6, 133.1, 132.4, 131.8, 127.1, 119.0, 110.3, 108.1, 101.7, 51.8, 51.6, 47.7, 45.8, 42.8, 42.3, 33.3, 20.7, 18.8, 17.6.

Example 26

3-amino-1-[{4-(2,4,5-trimethylphenyl)piperazin-1-yl}propanoyl]-6-N-(p-tolyl)-4,5,6,7-tetrahydro-1H-pyrazolo[3,4-c]pyridin-7-one (Compound 26)

A target compound (107.5 mg, 0.214 mmol, 53.7%) was yielded as solid in the same manner as Example 1 by reacting 3-amino-5,6-dihydro-6-N-(p-tolyl)-1H-pyrazolo[3,4-c]pyridin-7(4H)-one (97 mg, 0.4 mmol) with potassium carbonate (82.9 mg, 0.6 mmol) and 3-chloro-1-{4-(2,4,5-trimethylphenyl)piperazin-1-yl}propan-1-one (129.7 mg, 0.44 mmol).

$^1$H NMR (CDCl$_3$, 300 MHz) δ 7.22-7.15 (m, 4H), 6.96 (s, 1H), 6.74 (s, 1H), 4.55 (s, 2H, NH$_2$), 4.37 (t, J=4.9 Hz, 2H), 3.91 (t, J=6.4 Hz, 2H), 3.70 (br, 2H), 3.55 (br, 2H), 3.00 (t, J=4.9 Hz, 2H), 2.83-2.78 (m, 4H), 2.72 (t, J=6.4 Hz, 2H), 2.33 (s, 3H), 2.24 (s, 3H), 2.19 (s, 3H), 2.18 (s, 3H).

$^{13}$C NMR (CDCl$_3$, 75 MHz) δ 169.6, 161.6, 148.4, 142.2, 141.9, 140.4, 135.8, 134.5, 132.4, 131.8, 129.8, 129.5, 125.5, 120.5, 102.1, 51.9, 51.7, 50.5, 45.9, 42.8, 42.5, 33.4, 21.0, 19.5, 18.9, 17.1.

Example 27

3-amino-1-[{4-(4-t-butylphenyl)piperazin-1-yl}propanoyl]-6-N-(p-tolyl)-4,5,6,7-tetrahydro-1H-pyrazolo[3,4-c]pyridin-7-one (Compound 27)

A target compound (173.3 mg, 0.336 mmol, 86.8%) was yielded as solid in the same manner as Example 1 by reacting 3-amino-5,6-dihydro-6-N-(p-tolyl)-1H-pyrazolo[3,4-c]pyridin-7(4H)-one (94 mg, 0.388 mmol) with potassium carbonate (80.4 mg, 0.582 mmol) and 1-{4-(4-t-butylphenyl)piperazin-1-yl}-3-chloropropan-1-one (131.5 mg, 0.426 mmol).

$^1$H NMR (CDCl$_3$, 300 MHz) δ 7.28 (d, J=8.7 Hz, 2H), 7.19-7.12 (m, 4H), 6.83 (d, J=8.7 Hz, 2H), 4.53 (s, 2H, NH$_2$), 4.36 (t, J=4.8 Hz, 2H), 3.82 (t, J=6.4 Hz, 2H), 3.68 (br, 2H), 3.54 (br, 2H), 3.04 (br, 4H), 2.97 (t, J=4.8 Hz, 2H), 2.65 (t, J=6.4 Hz, 2H), 2.31 (s, 3H), 1.28 (s, 9H).

$^{13}$C NMR (CDCl$_3$, 75 MHz) δ 169.6, 161.6, 148.4, 143.3, 142.2, 142.0, 140.5, 135.7, 129.4, 126.0, 125.5, 116.3, 102.2, 51.9, 49.6, 49.4, 45.3, 43.0, 41.8, 34.0, 33.3, 31.4, 21.0, 19.5.

Example 28

3-amino-1-[{4-(cyclohexylphenyl)piperazin-1-yl}propanoyl]-6-N-(p-tolyl)-4,5,6,7-tetrahydro-1H-pyrazolo[3,4-c]pyridin-7-one (Compound 28)

A target compound (136.1 mg, 0.251 mmol, 67.8%) was yielded as solid in the same manner as Example 1 by reacting 3-amino-5,6-dihydro-6-N-(p-tolyl)-1H-pyrazolo[3,4-c]pyridin-7(4H)-one (90 mg, 0.371 mmol) with potassium carbonate (76.8 mg, 0.556 mmol) and 3-chloro-1-{4-(4-cyclohexylphenyl)piperazin-1-yl}propan-1-one (136.6 mg, 0.408 mmol).

$^1$H NMR (CDCl$_3$, 300 MHz) δ 7.19-7.15 (m, 4H), 7.10 (d, J=8.6 Hz, 2H), 6.82 (d, J=8.5 Hz, 2H), 4.51 (s, 2H, NH$_2$), 4.35 (t, J=4.7 Hz, 2H), 3.82 (t, J=6.3 Hz, 2H), 3.70 (br, 2H), 3.54 (br, 2H), 3.03 (br, 4H), 2.97 (t, J=4.8 Hz, 2H), 2.66 (t, J=6.3 Hz, 2H), 2.42 (br, 1H), 2.31 (s, 3H), 1.81 (br, 4H), 1.73 (d, J=12.2 Hz, 1H), 1.43-1.20 (m, 5H).

$^{13}$C NMR (CDCl$_3$, 75 MHz) δ 169.6, 161.6, 148.8, 142.2, 141.9, 140.5, 140.4, 135.7, 129.4, 127.4, 125.5, 116.7, 102.2, 51.9, 49.8, 49.6, 45.4, 43.6, 42.9, 41.9, 34.6, 33.2, 26.9, 26.1, 21.0, 19.4.

Formulation Examples

The novel compound represented by Chemical Formula 1 according to the present disclosure may be prepared into various formulations depending on purposes. The followings are some non-limiting examples of formulations comprising the compound represented by Chemical Formula 1 as an active ingredient.

Formulation Example 1

Tablet (Direct Compounding)

The active ingredient (5.0 mg) was sieved, mixed with lactose (14.1 mg), crospovidone USNF (0.8 mg) and magnesium stearate (0.1 mg), and then compounded into a tablet.

Formulation Example 2

Tablet (Wet Granulation)

The active ingredient (5.0 mg) was sieved and mixed with lactose (16.0 mg) and starch (4.0 mg). After adding an adequate amount of Polysorbate 80 (0.3 mg) dissolved in pure water, the mixture was granulated. After drying, the resulting granule was sieved and mixed with colloidal silicon dioxide (2.7 mg) and magnesium stearate (2.0 mg). The granule was compounded into a tablet.

Formulation Example 3

Powder and Capsule

The active ingredient (5.0 mg) was sieved and mixed with lactose (14.8 mg), polyvinylpyrrolidone (10.0 mg) and magnesium stearate (0.2 mg). The resulting mixture was filled in a hard, No. 5 gelatin capsule using an adequate apparatus.

Formulation Example 4

Injection

The active ingredient (100 mg), mannitol (180 mg) and $Na_2HPO_4 \cdot 12H_2O$ (26 mg) were dissolved in distilled water (2974 mg).

Test Example

Anticancer Activity Screening Test

1) Culture of Cancer Cells

A-549 (human lung carcinoma), HT-29 (human colon adenocarcinoma), DU145 (human prostate cancer), SK-MEL-2 (human malignant melanoma) and SK-OV-3 (human ovary malignant ascites) cells were used to evaluate the anticancer activity of the test compounds. All the cancer cells are all tumors cells derived from human and were acquired from the Korean Cell Line Bank. RP MI 1640 medium containing 10% fetal bovine serum was used as a culture medium. Cell culturing was performed in a constant-temperature, constant-humidity incubator (37° C., 5% $CO_2$). Subculturing was performed once in 3 days, using 0.25% trypsin-1 mM EDTA.

2) Measurement of Anticancer Activity

The sulforhodamine B (SRS) assay, which was developed in 1989 by the National Cancer Institute to measure in vitro anticancer activity of drugs, was employed.

The subcultured cells were transferred using trypsin-EDTA solution to a 96-well microplate, at $5 \times 10^3$ cells per well, and then cultured in a $CO_2$ incubator for 24 hours. After removing the medium and adding a solution of the test compound (100 μL) diluted 4-fold, the cells were cultured for 48 hours. After immobilizing the cells by adding formalin solution (100 μL), they were washed 5 times with distilled water and then dried at room temperature. The cells were added with 0.4% SRS solution (100 μL), allowed to stand at room temperature for 30 minutes, and then washed 5 times with 1% acetic acid and then dried at room temperature. After completely lysing the cells by adding 10 mM Trizma base (pH 10.3, 200 μL) to each well, absorbance was measured at 520 nm.

In order to evaluate the activity of the test compound for the cancer cells, $GI_{50}$ was calculated according to Equation 1 or 2.

$$\text{Anticancer activity (\%)} = \frac{T_2 - T_0}{T_0} \times 100 \text{ (if } T_2 > T_0) \quad \text{Equation 1}$$

where $T_0$ is the number of cells before adding the test compound, and $T_2$ is the number of cells after adding the test compound and culturing for 48 hours.

$$\text{Anticancer activity (\%)} = \frac{T_2 - T_0}{C - T_0} \times 100 \text{ (if } T_2 \leq T_0) \quad \text{Equation 2}$$

where $T_0$ is the number of cells before adding the test compound, $T_2$ is the number of cells after adding the test compound and culturing for 48 hours, and C is the number of cells of a control group to which no test compound was added after culturing for 48 hours.

The concentration at which each test compound inhibits the growth of the cancer cells (inhibitory concentration) was computed from a data regression of the values calculated from Equation 1 or 2 using the Louts software. Then, $IC_{50}$ value was calculated from the inhibitory concentration. The results are shown in Table 1 and Table 2.

TABLE 1

| Test | Inhibition % (100 mM) for cancer cells | | | |
|---|---|---|---|---|
| compounds | DU-145 | HT-29 | HCT-116 | A375P |
| Compound 2 | 75.05 | 95.21 | 72.18 | 86.03 |
| Compound 3 | 21.27 | 38.19 | 9.95 | 38.1 |
| Compound 4 | 90.55 | 94.07 | 93.17 | 89.73 |
| Compound 7 | 95.97 | 96.75 | 97.39 | 97.62 |
| Compound 8 | 52.38 | 45.06 | 42.06 | 43.38 |
| Compound 9 | 80.02 | 90.54 | 92.19 | 95.03 |
| Compound 10 | 38.10 | 32.12 | 33.48 | 44.03 |
| Compound 12 | 85.77 | 90.68 | 96.57 | 97.26 |
| Compound 13 | 24.99 | 29.50 | 36.37 | 22.49 |
| Compound 15 | 72.19 | 74.12 | 79.42 | 89.14 |
| Compound 17 | 93.50 | 94.43 | 95.46 | 97.28 |
| Doxorubicin | 62.79 | 60.89 | N.D. | N.D. |

DU-145: human prostate cancer
HT-29: human colon adenocarcinoma
HCT-116: human colon cancer
A375P: human melanoma cancer

TABLE 2

| Test | $IC_{50}$ (μM) for cancer cells | | | |
|---|---|---|---|---|
| compounds | DU-145 | HT-29 | HCT-116 | A375P |
| Compound 17 | 0.40 ± 0.02 | 0.15 ± 0.01 | 0.34 ± 0.01 | 0.34 ± 0.03 |

As seen from Table 1 and Table 2 the 1,6-disubstituted-3-amino-4,5,6,7-tetrahydro-1H-pyrazolo[3,4-c]pyridin-7-one compound represented by Chemical Formula 1 according to the present disclosure exhibits cytotoxicity for various cancer cells and thus is useful as a novel anticancer agent.

The present disclosure has been described in detail with reference to specific embodiments thereof. However, it will be appreciated by those skilled in the art that various changes and modifications may be made in these embodiments without departing from the principles and spirit of the disclosure, the scope of which is defined in the appended claims and their equivalents.

What is claimed is:

1. A compound selected from a 1,6-disubstituted-3-amino-4,5,6,7-tetrahydro-1H-pyrazolo[3,4-c]pyridin-7-one compound represented by Chemical Formula 1 or a pharmaceutically acceptable salt thereof:

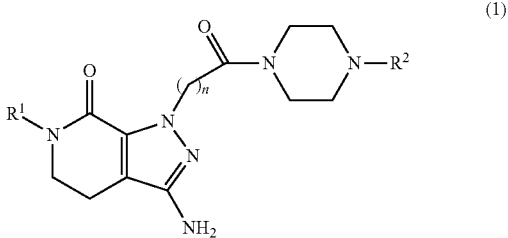

(1)

wherein n is an integer of 1, 2 or 3; $R^1$ and $R^2$, which are the same or different, are $R-(CH_2)_1-$, where R is phenyl, furyl, pyridyl or benzodioxol substituted or unsubstituted with 1 to 3 substituents selected from halo, $C_1$-$C_8$ alkyl, halo $C_1$-$C_8$ alkyl, $C_1$-$C_8$ alkoxy, amino, $C_1$-$C_8$ alkylamino and di($C_1$-$C_8$ alkyl)amino; and 1 is an integer of 0, 1, 2 or 3.

2. The compound according to claim 1, wherein n is an integer of 1, 2 or 3; and $R^1$ and $R^2$, which are the same or different, are phenyl, 3-chlorophenyl, 4-chlorophenyl, 2,3-dichlorophenyl, 2,3-difluorophenyl, 4-trifluoromethyl)phenyl, 2-methylphenyl, 3-methylphenyl, 4-methylphenyl, 4-t-butylphenyl, 4-cyclohexylphenyl, 2,3-dimethylphenyl, 2,4-dimethylphenyl, 2,4,5-trimethylphenyl, 4-methoxyphenyl, benzyl, 4-t-butylbenzyl, 2,4,6-trimethylbenzyl, 2,3,4-trimethoxybenzyl, (benzo[d][1,3]-dioxol-5-yl)methyl, furyl, furan-2-ylmethyl or pyridin-2-yl.

3. The compound according to claim 1, which is selected from: 3-amino-1-[{4-(2,3-dimethylphenyl)piperazin-1-yl}ethanoy]-6-N-(p-tolyl)-4,5,6,7-tetrahydro-1H-pyrazolo[3,4-c]pyridin-7-one (Compound 1), 3-amino-1-[{4-(2,3-dimethylphenyl)piperazin-1-yl}propanoyl]-6-N-(p-tolyl)-4,5,6,7-tetrahydro-1H-pyrazolo[3,4-c]pyridin-7-one (Compound 2), 3-amino-1-{(4-phenylpiperazin-1-yl)propanoyl}-6-N-(p-tolyl)-4,5,6,7-tetra-hydro-1H-pyrazolo[3,4-c]pyridin-7-one (Compound 3), 3-amino-1-[{4-(2,4-dimethylphenyl)piperazin-1-yl}propanoyl]-6-N-(p-tolyl)-4,5,6,7-tetrahydro-1H-pyrazolo[3,4-c]pyridin-7-one (Compound 4), 3-amino-1-[{4-((benzo[d][1,3]dioxol-5-yl)methyl)piperazin-1-yl)}propanoyl]-6-N-(p-tolyl)-4,5,6,7-tetrahydro-1H-pyrazolo[3,4-c]pyridin-7-one (Compound 5), 3-amino-1-[{4-(2,4,6-trimethyl benzyl)piperazin-1-yl}propanoyl]-6-N-(p-tolyl)-4,5,6,7-tetrahydro-1H-pyrazolo[3,4-c]pyridin-7-one (Compound 6), 3-amino-1-[{(4-4-t-butylbenzyl)piperazin-1-yl}propanoyl]-6-N-(p-tolyl)-4,-5,6,7-tetrahydro-1H-pyrazolo[3,4-c]pyridin-7-one (Compound 7), 3-amino-1-[{4-(2,3,4-trimethoxybenzyl)piperazin-1-yl}propanoyl]-6-N-(p-to-lyl)-4,5,6,7-tetrahydro-1H-pyrazolo[3,4-c]pyridin-7-one (Compound 8), 3-amino-1-[{4-(4-chlorophenyl)piperazin-1-yl}propanoyl]-6-N-(p-tolyl)-4,5,-6,7-tetrahydro-1H-pyrazolo[3,4-c]pyridin-7-one (Compound 9), 3-amino-1-[{4-(4-methoxyphenyl)piperazin-1-yl}propanoyl]-6-N-(p-tolyl)-4,-5,6,7-tetrahydro-1H-pyrazolo[3,4-c]pyridin-7-one (Compound 10), 3-amino-1-{(N-benzyl)piperazin-1-yl}-6-N-(p-methoxyphenyl)-4,5,6,7-tetrah-ydro-pyrazolo[3,4-c]pyridin-7-one (Compound 11), 3-amino-1-[{4-(2,4-dimethylphenyl)piperazin-1-yl}propanoyl]-6-N-(p-methox-yphenyl)-4,5,6,7-tetrahydro-1H-pyrazolo[3,4-c]pyridin-7-one (Compound 12), 3-amino-1-[{4-(2,4,6-trimethylbenzy)piperazin-1-yl}propanoyl]-6-N-(p-met-hoxyphenyl)-4,5,6,7-tetrahydro-1H-pyrazolo[3,4-c]pyridin-7-one (Compound 13), 3-amino-[{4-(2,3,4-trimethoxybenzyl)piperazin-1-yl}propanoyl]-6-N-(p-methoxyphenyl)-4,5,6,7-tetrahydro-1H-pyrazolo[3,4-c]pyridin-7-one (Compound 14), 3-amino-1-[{4-(2,4-dimethylphenyl)piperazin-1-yl}propanoyl]-6-N-phenyl-4,-5,6,7-tetrahydro-1H-pyrazolo[3,4-c]pyridin-7-one (Compound 15), 3-amino-1-[{4-(2,4,6-trimethylbenzy)piperazin-1-yl}propanoyl]-6-N-phenyl-4,5,6,7-tetrahydro-1H-pyrazolo[3,4-c]pyridin-7-one (Compound 16), 3-amino-1-[{4-(2,4-dimethylphenyl)piperazin-1-yl}propanoyl]-6-N-benzyl-4,-5,6,7-tetrahydro-1H-pyrazolo[3,4-c]pyridin-7-one (Compound 17), 3-amino-1-{(4-phenylpiperazin-1-yl)propanoyl}-6-N-{p-(dimethylamino)pheny-1}-4,5,6,7-tetrahydro-1H-pyrazolo[3,4-c]pyridin-7-one (Compound 18), 3-amino-1-[{4-(4-methoxyphenyl)piperazin-1-yl}propanoyl]-6-N-{p-(dimethyl-amino)phenyl}-4,5,6,7-tetrahydro-1H-pyrazolo[3,4-c]pyridin-7-one (Compound 19), 3-amino-1-{(4-phenylpiperazin-1-yl)propanoyl}-6-N-{(furan-2-yl)methyl-1}-4,5,6,7-tetrahydro-1H-pyrazolo[3,4-c]pyridin-7-one (Compound 20), 3-amino-1-[{4-(4-methoxyphenyl)piperazin-1-yl}propanoyl]-6-N-{(furan-2-yl-)methyl}-4,5,6,7-tetrahydro-1H-pyrazolo[3,4-c]pyridin-7-one (Compound 21), 3-amino-1-{4-(2-pyridinylpiperazin-1-yl)propanoyl}-6-N-p-tolyl-4,5,6,7-tetrahydro-1H-pyrazolo[3,4-c]pyridin-7-one (Compound 22), 3-amino-1-{4-(2-pyridinylpiperazin-1-yl)propanoyl}-6-N-{(furan-2-yl)methyl-1}-4,5,6,7-tetrahydro-H-pyrazolo[3,4-c]pyridin-7-one (Compound 23), 3-amino-1-[{4-(4-trifluoromethylphenyl)piperazin-1-yl}propanoyl]-6-N-(p-tolyl)-4,5,6,7-tetrahydro-1H-pyrazolo[3,4-c]pyridin-7-one (Compound 24), 3-amino-1-[{4-(2,4-dimethylphenyl)piperazin-1-yl}propanroyl]-6-N-{(furan-2-yl)methyl}-4,5,6,7-tetrahydro-1H-pyrazolo[3,4-c]pyridin-7-one (Compound 25), 3-amino-1-[{4-(2,4,5-trimethylphenyl)piperazin-1-yl}propanoyl]-6-N-(-p-tolyl)-4,5,6,7-tetrahydro-1H-pyrazolo[3,4-c]pyridin-7-one (Compound 26), 3-amino-1-[{4-(4-t-butylphenyl)piperazin-1-yl}propanoyl]-6-N-(p-tolyl)-4,-5,6,7-tetrahydro-1H-pyrazolo[3,4-c]pyridin-7-one (Compound 27), 3-amino-1-[{4-(cyclohexyphenyl)piperazin-1-yl}propanoyl]-6-N-(p-tolyl)-4,-5,6,7-tetrahydro-1H-pyrazolo[3,4-c]pyridin-7-one (Compound 28), and pharmaceutically acceptable salts thereof.

4. An anticancer pharmaceutical composition comprising the compound according to claim 1 as an effective ingredient.

5. A method for preparing a 1,6-disubstituted-3-amino-4,5,6,7-tetralydro-1:1-pyrazolo[3,4-c]pyridin-7-one compound represented by Chemical Formula 1, comprising alkylating a 3-amino compound represented by Chemical Formula 2 with a haloalkylcarbonyl piperazine compound represented by Chemical Formula 3 to prepare the compound represented by Chemical Formula 1:

(2)
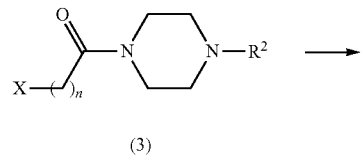
(3)
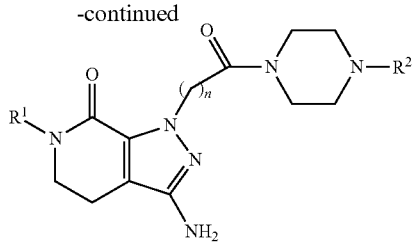
(1)
wherein n, $R^1$, and $R^2$ are the same as defined in claim 1 and X is a halogen atom.
6. An anticancer pharmaceutical composition comprising the compound according to claim 2 as an effective ingredient.
7. An anticancer pharmaceutical composition comprising the compound according to claim 3 as an effective ingredient.
* * * * *